US009833130B2

(12) United States Patent
Schaeffer et al.

(10) Patent No.: US 9,833,130 B2
(45) Date of Patent: Dec. 5, 2017

(54) IRRIGATION DEVICES ADAPTED TO BE USED WITH A LIGHT SOURCE FOR THE IDENTIFICATION AND TREATMENT OF BODILY PASSAGES

(71) Applicant: Cook Medical Technologies LLC, Bloomington, IN (US)

(72) Inventors: Darin Schaeffer, Bloomington, IN (US); Patrick C. Melder, Marietta, GA (US); Thomas Cherry, Covington, LA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 316 days.

(21) Appl. No.: 14/809,328

(22) Filed: Jul. 27, 2015

(65) Prior Publication Data

US 2015/0327945 A1 Nov. 19, 2015

Related U.S. Application Data

(63) Continuation of application No. 13/555,453, filed on Jul. 23, 2012, now Pat. No. 9,089,631.
(Continued)

(51) Int. Cl.
*A61B 1/12* (2006.01)
*A61B 1/00* (2006.01)
(Continued)

(52) U.S. Cl.
CPC ......... *A61B 1/00165* (2013.01); *A61B 1/015* (2013.01); *A61B 1/233* (2013.01);
(Continued)

(58) Field of Classification Search
CPC ......... A61B 1/015; A61B 1/0051; A61B 1/06; A61B 1/0661; A61B 1/07; A61B 1/0669; A61B 1/0676
(Continued)

(56) References Cited

U.S. PATENT DOCUMENTS 2,649,092 A 8/1953 Wallace
3,081,767 A 3/1963 Hett
(Continued)

FOREIGN PATENT DOCUMENTS

CA 2403030 3/2003
EP 0163266 12/1985
(Continued)

OTHER PUBLICATIONS

Non-final Office Action dated Sep. 15, 2009 U.S. Appl. No. 11/800,292.
(Continued)

*Primary Examiner* — Ellen C Hammond
*Assistant Examiner* — Christina Negrellirodrigue
(74) *Attorney, Agent, or Firm* — Buchanan Van Tuinen LLC

(57) ABSTRACT

Devices and methods of identifying and treating bodily passages, such as sinus cavities, are provided. More particularly, irrigation devices and methods useful in the identification and treatment of bodily passages, such as sinus cavities, are provided. The irrigation devices comprise an elongate tubular member and an optical fiber which assist with the transcutaneous identification and/or treatment of a bodily passage.

20 Claims, 7 Drawing Sheets

Related U.S. Application Data

(60) Provisional application No. 61/510,611, filed on Jul. 22, 2011.

(51) Int. Cl.
*A61B 1/015* (2006.01)
*A61B 1/233* (2006.01)
*A61M 3/02* (2006.01)
*A61B 90/30* (2016.01)

(52) U.S. Cl.
CPC ............ *A61B 90/30* (2016.02); *A61M 3/0279* (2013.01); *A61B 2090/306* (2016.02); *A61B 2217/005* (2013.01); *A61M 2205/587* (2013.01); *A61M 2210/0681* (2013.01)

(58) Field of Classification Search
USPC ....... 600/139, 156, 160, 174, 178, 182, 249; 604/19, 20, 21, 27, 35, 95.03
See application file for complete search history.

(56) References Cited

U.S. PATENT DOCUMENTS

| | | |
|---|---|---|
| 3,521,620 A | 7/1970 | Cook |
| 3,625,200 A | 12/1971 | Muller |
| 4,551,129 A | 11/1985 | Coleman et al. |
| 4,696,544 A | 9/1987 | Costella |
| 4,719,924 A | 1/1988 | Crittenden et al. |
| 4,726,374 A | 2/1988 | Bales et al. |
| 4,790,812 A | 12/1988 | Hawkins et al. |
| 4,826,087 A | 5/1989 | Chinery |
| 4,834,709 A | 5/1989 | Banning et al. |
| 4,841,976 A | 6/1989 | Packard et al. |
| 4,886,067 A | 12/1989 | Palermo |
| 5,125,395 A | 6/1992 | Adair |
| 5,308,318 A | 5/1994 | Plassche, Jr. |
| 5,380,305 A | 1/1995 | Ghouri |
| 5,441,483 A | 8/1995 | Avitall |
| 5,447,503 A | 9/1995 | Miller |
| 5,460,616 A | 10/1995 | Weinstein et al. |
| 5,470,330 A | 11/1995 | Goldenberg et al. |
| 5,477,860 A | 12/1995 | Essen-Moller |
| 5,480,382 A | 1/1996 | Hammerslag et al. |
| 5,489,278 A | 2/1996 | Abrahamson |
| 5,509,900 A | 4/1996 | Kirkman |
| 5,514,128 A | 5/1996 | Hillsman et al. |
| 5,522,400 A | 6/1996 | Williams |
| 5,534,007 A | 7/1996 | Germain et al. |
| 5,642,736 A | 7/1997 | Avitall |
| 5,643,171 A | 7/1997 | Bradshaw et al. |
| 5,658,301 A | 8/1997 | Lemaitre et al. |
| 5,674,197 A | 10/1997 | van Muiden et al. |
| 5,685,858 A | 11/1997 | Kawand |
| 5,718,684 A | 2/1998 | Gupta |
| 5,738,664 A | 4/1998 | Erskine et al. |
| 5,769,821 A | 6/1998 | Abrahamson et al. |
| 5,807,398 A | 9/1998 | Shaknovich |
| 5,820,546 A | 10/1998 | Ouchi |
| 5,865,800 A | 2/1999 | Mirarchi et al. |
| 5,908,403 A | 6/1999 | Bosma et al. |
| 5,916,214 A | 6/1999 | Cosio et al. |
| 5,931,811 A | 8/1999 | Haissaguerre et al. |
| 5,938,582 A | 8/1999 | Ciamacco et al. |
| 5,954,050 A | 9/1999 | Christopher |
| 5,989,241 A | 11/1999 | Plishka et al. |
| 6,033,378 A | 3/2000 | Lundquist et al. |
| 6,066,125 A | 5/2000 | Webster, Jr. |
| 6,071,263 A | 6/2000 | Kirkman |
| 6,096,036 A | 8/2000 | Bowe et al. |
| 6,117,386 A | 9/2000 | Stiger |
| 6,123,699 A | 9/2000 | Webster, Jr. |
| 6,126,649 A | 10/2000 | VanTassel et al. |
| 6,159,158 A | 12/2000 | Lowe |
| 6,159,177 A | 12/2000 | Amos, Jr. et al. |
| 6,183,463 B1 | 2/2001 | Webster, Jr. |
| 6,206,870 B1 | 3/2001 | Kanner |
| 6,226,432 B1 | 5/2001 | Gonda |
| 6,261,284 B1 | 7/2001 | Ouchi |
| 6,338,735 B1 | 1/2002 | Stevens |
| 6,383,206 B1 | 5/2002 | Gillick et al. |
| 6,447,530 B1 | 9/2002 | Ostrovsky et al. |
| 6,450,988 B1 | 9/2002 | Bradshaw |
| 6,485,500 B1 | 11/2002 | Kokish et al. |
| 6,491,662 B1 | 12/2002 | Liprie et al. |
| 6,500,147 B2 | 12/2002 | Omaleki et al. |
| 6,500,167 B1 | 12/2002 | Webster, Jr. |
| 6,500,182 B2 | 12/2002 | Foster |
| 6,508,833 B2 | 1/2003 | Pavcnik et al. |
| 6,527,737 B2 | 3/2003 | Kaneshige |
| 6,530,913 B1 | 3/2003 | Giba et al. |
| 6,533,783 B1 | 3/2003 | Tollner |
| 6,558,349 B1 | 5/2003 | Kirkman |
| 6,572,610 B2 | 6/2003 | Kovalcheck et al. |
| 6,629,987 B1 | 10/2003 | Gambale |
| 6,673,060 B1 | 1/2004 | Fleming, III |
| 6,679,860 B2 | 1/2004 | Stiger |
| 6,692,484 B1 | 2/2004 | Karpiel et al. |
| 6,695,858 B1 | 2/2004 | Dubrul et al. |
| 6,755,812 B2 | 6/2004 | Peterson et al. |
| 6,829,497 B2 | 12/2004 | Mogul |
| 6,918,929 B2 | 7/2005 | Udipi et al. |
| 6,932,829 B2 | 8/2005 | Majercak |
| 7,037,290 B2 | 5/2006 | Gardeski et al. |
| 7,056,314 B1 | 6/2006 | Florio et al. |
| 7,144,408 B2 | 12/2006 | Keegan et al. |
| 7,150,713 B2 | 12/2006 | Shener et al. |
| 7,232,462 B2 | 6/2007 | Schaeffer |
| 7,269,453 B2 | 9/2007 | Mogul |
| 7,273,468 B2 | 9/2007 | Bedell |
| 7,351,214 B2 | 4/2008 | Burgermeister |
| 7,361,168 B2 | 4/2008 | Makower et al. |
| 7,410,480 B2 | 8/2008 | Muni et al. |
| 7,462,175 B2 | 12/2008 | Chang et al. |
| 7,500,971 B2 | 3/2009 | Chang et al. |
| 7,503,914 B2 | 3/2009 | Coleman et al. |
| 7,520,876 B2 | 4/2009 | Ressemann et al. |
| 7,559,925 B2 | 7/2009 | Goldfarb et al. |
| 7,641,630 B2 | 1/2010 | Accisano, III et al. |
| 7,645,272 B2 | 1/2010 | Chang et al. |
| 7,654,997 B2 | 2/2010 | Makower et al. |
| 7,658,305 B2 | 2/2010 | Voegele et al. |
| 7,678,099 B2 | 3/2010 | Ressemann et al. |
| 7,691,095 B2 | 4/2010 | Bednarek et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,331 B2 | 6/2010 | Accisano, III et al. |
| 7,740,608 B2 | 6/2010 | Lampropoulos et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,785,252 B2 | 8/2010 | Danitz et al. |
| 7,785,315 B1 | 8/2010 | Muni et al. |
| 7,803,130 B2 | 9/2010 | Ryan et al. |
| 7,803,150 B2 | 9/2010 | Chang et al. |
| 7,811,277 B2 | 10/2010 | Boulais |
| 7,854,744 B2 | 12/2010 | Becker |
| 7,867,218 B1 | 1/2011 | Voda |
| 7,879,061 B2 | 2/2011 | Keith et al. |
| 7,892,233 B2 | 2/2011 | Hall et al. |
| 7,909,814 B2 | 3/2011 | Accisano, III et al. |
| 7,909,862 B2 | 3/2011 | Garrison |
| 7,918,871 B2 | 4/2011 | Truitt et al. |
| 7,935,108 B2 | 5/2011 | Baxter et al. |
| 7,959,601 B2 | 6/2011 | McDaniel et al. |
| 7,959,644 B2 | 6/2011 | Shriver |
| 8,029,461 B2 | 10/2011 | Thielen et al. |
| 8,066,664 B2 | 11/2011 | LaDuca et al. |
| 8,070,693 B2 | 12/2011 | Ayala et al. |
| 8,083,879 B2 | 12/2011 | Swinehart et al. |
| 8,088,101 B2 | 1/2012 | Chang et al. |

(56) References Cited

U.S. PATENT DOCUMENTS

| | | |
|---|---|---|
| 8,090,433 B2 | 1/2012 | Makower et al. |
| 8,100,933 B2 | 1/2012 | Becker |
| 8,114,062 B2 | 2/2012 | Muni et al. |
| 8,118,803 B1 | 2/2012 | Chow |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,182,467 B2 | 5/2012 | Nguyen et al. |
| 8,216,210 B2 | 7/2012 | Ostrovsky et al. |
| 8,241,266 B2 | 8/2012 | Keith et al. |
| 8,277,478 B2 | 10/2012 | Drontle et al. |
| 8,282,667 B2 | 10/2012 | Drontle et al. |
| 8,317,816 B2 | 11/2012 | Becker |
| 8,369,923 B2 | 2/2013 | de la Rama et al. |
| 8,388,642 B2 | 3/2013 | Muni et al. |
| 8,403,977 B2 | 3/2013 | Case |
| 8,414,473 B2 | 4/2013 | Jenkins et al. |
| 8,425,457 B2 | 4/2013 | John et al. |
| 8,425,466 B2 | 4/2013 | Sargent, Jr. |
| 8,430,864 B2 | 4/2013 | Schultz |
| 8,435,290 B2 | 5/2013 | Clifford et al. |
| 8,496,645 B2 | 7/2013 | Eells et al. |
| 8,535,310 B2 | 9/2013 | Hardin, Jr. et al. |
| 8,535,349 B2 | 9/2013 | Chen et al. |
| 8,603,185 B2 | 12/2013 | Shah et al. |
| 8,657,805 B2 | 2/2014 | Peh et al. |
| 8,734,426 B2 | 5/2014 | Ahmed et al. |
| 8,740,843 B2 | 6/2014 | Eaton et al. |
| 8,758,231 B2 | 6/2014 | Bunch et al. |
| 9,089,631 B2 | 7/2015 | Schaeffer et al. |
| 9,192,710 B2 | 11/2015 | Feng et al. |
| 2001/0039450 A1 | 11/2001 | Pavcnik et al. |
| 2002/0115983 A1 | 8/2002 | Sekino et al. |
| 2003/0004460 A1 | 1/2003 | Bedell |
| 2003/0032977 A1 | 2/2003 | Brady |
| 2003/0050694 A1 | 3/2003 | Heneveld et al. |
| 2003/0216711 A1 | 11/2003 | Rabiner et al. |
| 2004/0087965 A1 | 5/2004 | Hebert et al. |
| 2004/0087996 A1 | 5/2004 | Forcucci et al. |
| 2004/0225322 A1 | 11/2004 | Garrison et al. |
| 2005/0038412 A1 | 2/2005 | Rabiner et al. |
| 2005/0159728 A1 | 7/2005 | Armour et al. |
| 2005/0171592 A1 | 8/2005 | Majercak |
| 2005/0256377 A1 | 11/2005 | Deppmeier et al. |
| 2005/0256452 A1 | 11/2005 | DeMarchi et al. |
| 2006/0063973 A1 | 3/2006 | Makower et al. |
| 2007/0083132 A1 | 4/2007 | Sharrow |
| 2007/0093781 A1 | 4/2007 | Kugler et al. |
| 2007/0129751 A1 | 6/2007 | Muni et al. |
| 2007/0167682 A1 | 7/2007 | Goldfarb et al. |
| 2007/0208252 A1 | 9/2007 | Makower |
| 2007/0219464 A1 | 9/2007 | Davis et al. |
| 2007/0250105 A1 | 10/2007 | Ressemann et al. |
| 2007/0282305 A1 | 12/2007 | Goldfarb et al. |
| 2007/0293727 A1 | 12/2007 | Goldfarb et al. |
| 2008/0015472 A1 | 1/2008 | Ressemann et al. |
| 2008/0015544 A1 | 1/2008 | Keith et al. |
| 2008/0097154 A1 | 4/2008 | Makower et al. |
| 2008/0103521 A1 | 5/2008 | Makower et al. |
| 2008/0119693 A1 | 5/2008 | Makower et al. |
| 2008/0125756 A1 | 5/2008 | Dicarlo et al. |
| 2008/0132938 A1 | 6/2008 | Chang et al. |
| 2008/0172033 A1 | 7/2008 | Keith et al. |
| 2008/0183128 A1* | 7/2008 | Morriss ............... A61M 3/0283 604/35 |
| 2008/0195041 A1 | 8/2008 | Goldfarb et al. |
| 2008/0228085 A1 | 9/2008 | Jenkins et al. |
| 2008/0243067 A1 | 10/2008 | Rottenberg et al. |
| 2008/0249483 A1 | 10/2008 | Slenker et al. |
| 2008/0262308 A1 | 10/2008 | Prestezog et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0287918 A1 | 11/2008 | Rosenman et al. |
| 2008/0319424 A1 | 12/2008 | Muni et al. |
| 2009/0030274 A1 | 1/2009 | Goldfarb et al. |
| 2009/0043299 A1 | 2/2009 | Racz |
| 2009/0093823 A1 | 4/2009 | Chang et al. |
| 2009/0187098 A1 | 7/2009 | Makower et al. |
| 2009/0198153 A1 | 8/2009 | Shriver |
| 2009/0198216 A1 | 8/2009 | Muni et al. |
| 2009/0216196 A1 | 8/2009 | Drontle et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2009/0326450 A1 | 12/2009 | Ostrovsky et al. |
| 2010/0010309 A1 | 1/2010 | Kitagawa |
| 2010/0030113 A1 | 2/2010 | Morriss et al. |
| 2010/0042046 A1 | 2/2010 | Chang et al. |
| 2010/0076269 A1 | 3/2010 | Makower et al. |
| 2010/0099946 A1 | 4/2010 | Jenkins et al. |
| 2010/0106141 A1 | 4/2010 | Osypka et al. |
| 2010/0114066 A1 | 5/2010 | Makower et al. |
| 2010/0168511 A1 | 7/2010 | Muni et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0211007 A1 | 8/2010 | Lesch, Jr. et al. |
| 2010/0217261 A1 | 8/2010 | Watson |
| 2010/0262075 A1 | 10/2010 | Danitz et al. |
| 2010/0268087 A1 | 10/2010 | Hirota |
| 2010/0268245 A1 | 10/2010 | Chang et al. |
| 2010/0274188 A1 | 10/2010 | Chang et al. |
| 2010/0280316 A1 | 11/2010 | Dietz et al. |
| 2010/0298862 A1 | 11/2010 | Chang et al. |
| 2010/0331776 A1 | 12/2010 | Salahieh et al. |
| 2011/0004057 A1 | 1/2011 | Goldfarb et al. |
| 2011/0009700 A1 | 1/2011 | Ostrovsky et al. |
| 2011/0040269 A1 | 2/2011 | Cline |
| 2011/0060214 A1 | 3/2011 | Makower |
| 2011/0071349 A1 | 3/2011 | Drontle et al. |
| 2011/0112476 A1 | 5/2011 | Kauphusman et al. |
| 2011/0112512 A1 | 5/2011 | Muni et al. |
| 2011/0160740 A1 | 6/2011 | Makower et al. |
| 2011/0190831 A1 | 8/2011 | Mafi et al. |
| 2011/0218492 A1 | 9/2011 | McDaniel et al. |
| 2011/0224652 A1 | 9/2011 | Drontle et al. |
| 2011/0264134 A1 | 10/2011 | Drontle et al. |
| 2011/0288477 A1 | 11/2011 | Ressemann et al. |
| 2011/0313392 A1 | 12/2011 | Varghese et al. |
| 2012/0010646 A1 | 1/2012 | Keith et al. |
| 2012/0046664 A1 | 2/2012 | McGuckin, Jr. et al. |
| 2012/0071824 A1 | 3/2012 | Chang et al. |
| 2012/0101441 A1 | 4/2012 | Sargent, Jr. |
| 2012/0116254 A1 | 5/2012 | Morriss |
| 2012/0136207 A1 | 5/2012 | Goldfarb et al. |
| 2012/0162401 A1 | 6/2012 | Melder et al. |
| 2012/0172912 A1 | 7/2012 | Ressemann et al. |
| 2012/0184983 A1 | 7/2012 | Chang et al. |
| 2012/0190973 A1 | 7/2012 | Ressemann et al. |
| 2012/0197240 A1 | 8/2012 | Smith et al. |
| 2012/0238952 A1 | 9/2012 | Mitchell et al. |
| 2012/0245419 A1 | 9/2012 | Makower et al. |
| 2012/0265055 A1 | 10/2012 | Melsheimer et al. |
| 2012/0265094 A1 | 10/2012 | Goldfarb et al. |
| 2012/0283625 A1 | 11/2012 | Keith et al. |
| 2013/0041314 A1 | 2/2013 | Dillon |
| 2013/0046138 A1 | 2/2013 | McLawhorn |
| 2013/0096605 A1 | 4/2013 | Becker |
| 2013/0103004 A1 | 4/2013 | Gray et al. |
| 2013/0137920 A1 | 5/2013 | Schaeffer et al. |
| 2013/0225937 A1 | 8/2013 | Schaeffer et al. |
| 2013/0226146 A1 | 8/2013 | Tekulve |
| 2013/0238003 A1 | 9/2013 | Fischer et al. |
| 2014/0088355 A1 | 3/2014 | Schaeffer |
| 2014/0243615 A1 | 8/2014 | Schaeffer et al. |
| 2016/0030694 A1 | 2/2016 | Gingles et al. |

FOREIGN PATENT DOCUMENTS

| | | |
|---|---|---|
| EP | 2368481 | 9/2011 |
| EP | 2522386 | 11/2012 |
| EP | 2710949 | 3/2014 |

(56) References Cited

FOREIGN PATENT DOCUMENTS

| GB | 2465621 | 6/2010 |
|---|---|---|
| WO | WO9843530 | 10/1998 |
| WO | WO0126726 | 4/2001 |
| WO | WO0170308 | 9/2001 |
| WO | WO03001986 | 1/2003 |
| WO | WO2006020180 | 2/2006 |
| WO | WO2008045242 | 4/2008 |
| WO | WO2011082074 | 7/2011 |
| WO | WO2011084655 | 7/2011 |
| WO | WO2013016275 | 1/2013 |
| WO | WO2014134257 | 9/2014 |

OTHER PUBLICATIONS

EyeMAX CCD Laparscopes [online brochure]. Richard Wolf GmbH [retrieved Nov. 15, 2013]. Retrieved from the internet: URL: http://www.richard-wolf.com/uploads/media/A_658_Eyemax_GB_I07.pdf. pp. 1-8.

EyeMAX Flexible LED Cystoscope [online brochure]. Richard Wolf GmbH [retrieved Nov. 15, 2013]. Retrieved from the internet: URL: http://www.richardwolfusa.com/fileadmin/images/content/USA_data/PDF_documents/Urology/Flexible_LED_Digital_Cystoscope_brochure_01312013.pdf. pp. 1-4.

Olympus Naso-laryngoscopes. Olympus. Retrieved from the Internet: URL: www.olympuskeymed.com, pp. 1-3.

XprESS Multi-Sinus Dilation Tool Using Bending Tool. Instructions for Use, Entellus Medical, Sep. 2011, pp. 1-7.

XprESS Multi-Sinus Dilation Tool. Instructions for Use, Entellus Medical, May 2011, pp. 1-7.

A trial study of RhinoSleep for the diagnosis of sleep apnea. Psychiatry and Clinical Neurosciences. Jun. 2001, pp. 1-2.

E.G. Scan—Trans-nasal, disposable system for upper GI screening [online brochure]. SynMed Ltd. [retrieved Jun. 4, 2014]. Retrieved from the Internet: URL: http://www.synmed.co.uk/products/eg_scan/pdf/SynMed_E.G.Scan_Brochure.pdf.

Drug-induced Sleep Endoscopy webpage [online], Eric J. Kezirian [retrieved Nov. 14, 2013]. Retrieved from the internet: URL: http://www.sleep-doctor.com/surgical-treatment-overview/drug-induced-sleep-endoscopy/.

EyeMax webpage [online], Richard Wolf [retrieved Nov. 14, 2013]. Retrieved from the internet: URL: http://www.richard-wolf.com/en/human-medicine/visualisation/video-endoscopes/ccd-endoscopes.html.

European Patent Office, Extended European Search Report, for International Application No. 13185810.2, dated Jan. 7, 2014, pp. 1-5.

International Searching Authority. International Search Report and Written Opinion, for International App. No. PCT/US2014/018878, dated Jun. 11, 2014. p. 1-12.

European Patent Office, European Search Report for application No. 12194127.2 dated Apr. 9, 2013, p. 1-5.

European Patent Office, Extended European Search Report for application No. 12194127.2 dated Jul. 25, 2013, p. 1-8.

International Bureau of WIPO, International Preliminary Report on Patentability for Int. App. No. PCT/US2012/047830, dated Jan. 28, 2014, pp. 1-6.

International Searching Authority, International Search Report and Written Opinion for International Application No. PCT/US2012/047830, dated Oct. 30, 2012.

\* cited by examiner

IRRIGATION DEVICES ADAPTED TO BE USED WITH A LIGHT SOURCE FOR THE IDENTIFICATION AND TREATMENT OF BODILY PASSAGES

RELATED APPLICATIONS

This application is a continuation of U.S. patent application Ser. No. 13/555,453, filed Jul. 23, 2012, and claims the benefit of U.S. Provisional Application No. 61/510,611, filed on Jul. 22, 2011. The entire disclosure of each of these related applications is hereby incorporated into this disclosure by reference.

FIELD

The invention relates generally to the field of medical devices. More particularly, the invention relates to irrigation devices useful in the identification and treatment of bodily passages, such as sinus cavities. The invention also relates to methods of identifying and treating bodily passages.

BACKGROUND

It is sometimes necessary or otherwise desirable to aspirate and/or flush bodily passages, such as sinus cavities, using a catheter. For example, when sinus cavities become infected, sinus irrigation provides an approach to address the infection. In conventional sinus irrigation procedures, a caregiver navigates a catheter over a previously-placed guidewire. Prior to irrigation, the caregiver must verify positioning of the catheter and/or guidewire using separate visualization equipment, such as a laryngoscope, fluoroscopy, or other suitable devices or techniques. This complicates the procedure by requiring the placement of multiple devices within the area of treatment and may provide less than ideal information about the area to be irrigated.

To facilitate position verification, lighted guidewires have been developed to facilitate visualization of the guidewire prior to irrigation. However, the use of such guidewires presents significant drawbacks. For example, while the guidewire can be visualized transcutaneously following placement in the sinus cavity, the light of the guidewire is blocked once the catheter is tracked over the tip of the guidewire, preventing the user from confirming final placement of the catheter prior to irrigating the sinus. Furthermore, the lighted guidewire does not convey any information to the user about the location of the catheter or the area of the cavity that will be treated during the irrigation procedure.

Therefore, a need exists for improved devices and methods of identifying and treating bodily passages.

SUMMARY

Several exemplary irrigation devices adapted to be used with a light source for the identification and treatment of bodily passages, such as sinus cavities, are described herein. In addition, several exemplary methods of identifying and treating bodily passages, such as sinus cavities, are described herein. In particular, irrigation devices including an elongate tubular member and an optical fiber are provided.

Irrigation devices with various elongate tubular member configurations are described, including elongate tubular members with single or double lumen configurations. Other examples include irrigation devices with multiple elongate tubular members. Further examples include elongate tubular members which define one or more apertures and/or curves and include a soft distal tip.

Irrigation devices with various optical fiber configurations are also described, including examples that have one or more optical fibers disposed within a lumen of an elongate tubular member. Other examples include configurations in which one or more optical fibers are disposed within lumens defined by the wall of the elongate tubular member and/or embedded within the wall of the elongate tubular member.

Additional understanding of the devices and methods contemplated and/or claimed by the inventor can be gained by reviewing the detailed description of exemplary embodiments, presented below, and the referenced drawings.

BRIEF DESCRIPTION OF THE DRAWINGS

FIG. 1A is a sectional view of the light emitting irrigation device in FIG. 1, taken along line 1A-1A.

FIG. 2A is a sectional view of the light emitting irrigation device in FIG. 2, taken along line 2A-2A.

FIG. 3A is a sectional view of the light emitting irrigation device in FIG. 3, taken along line 3A-3A.

FIG. 3B is a sectional view of the light emitting irrigation device in FIG. 3, taken along line 3B-3B.

FIG. 4A is a sectional view of the light emitting irrigation device in FIG. 4, taken along line 4A-4A.

DETAILED DESCRIPTION

The following detailed description and the appended drawings are provided to describe and illustrate exemplary embodiments of the invention for the purpose of enabling one of ordinary skill in the relevant art to make and use the invention. The description and drawings are not intended to limit the scope of the invention, or its protection, in any manner.

As used herein, the terms "proximal" and "distal" are used to describe opposing axial ends of the particular elements or features being described. The term "bodily passage" refers to any passage within the body of an animal, including, but not limited to humans, and includes elongate passages, such as blood vessels, and cavities, such as the sinus cavities. The term "irrigation" refers to aspiration and/or flushing of bodily passages. The term "attached" refers to the fixed, releasable, or integrated association of two or more elements and/or devices. Thus, the term "attached" includes releasably attaching or fixedly attaching two or more elements and/or devices.

Figure 1:
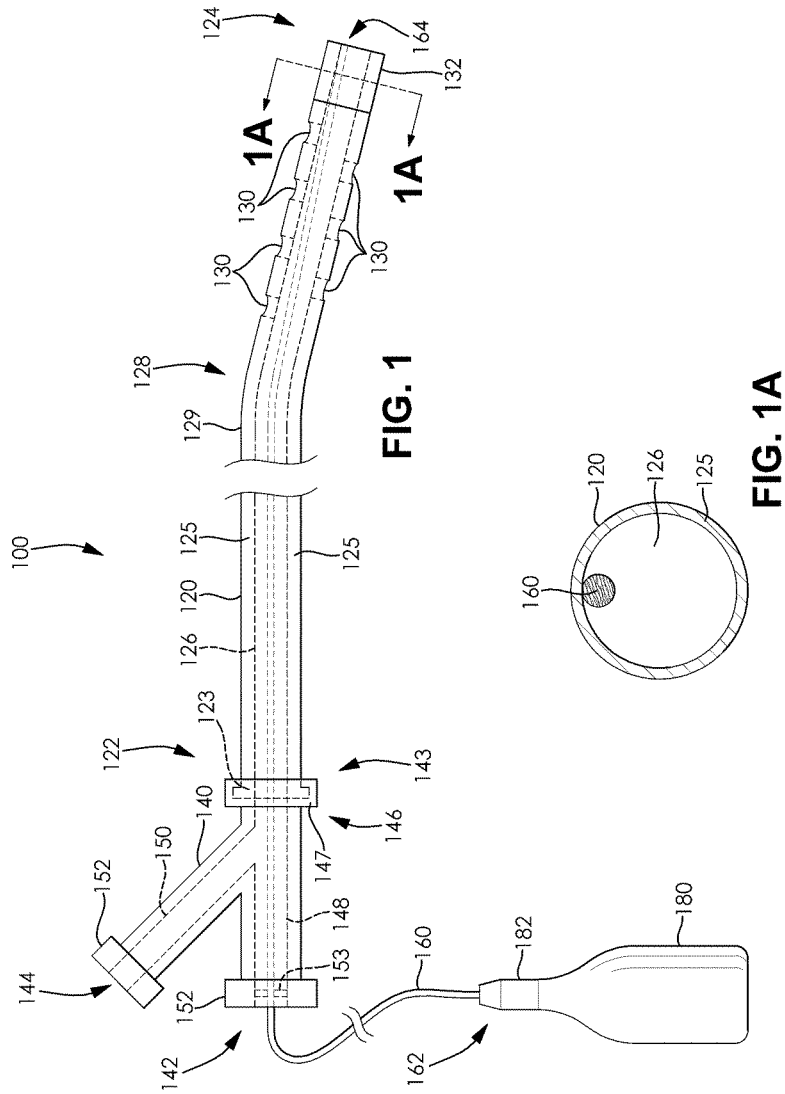
FIG. 1 is a side view of an exemplary light emitting irrigation device.

FIGS. 1 and 1A illustrate an exemplary light emitting irrigation device 100. The light emitting irrigation device 100 comprises an elongate tubular member 120, an adapter 140, an optical fiber 160, and a light source 180.

Figure 6:
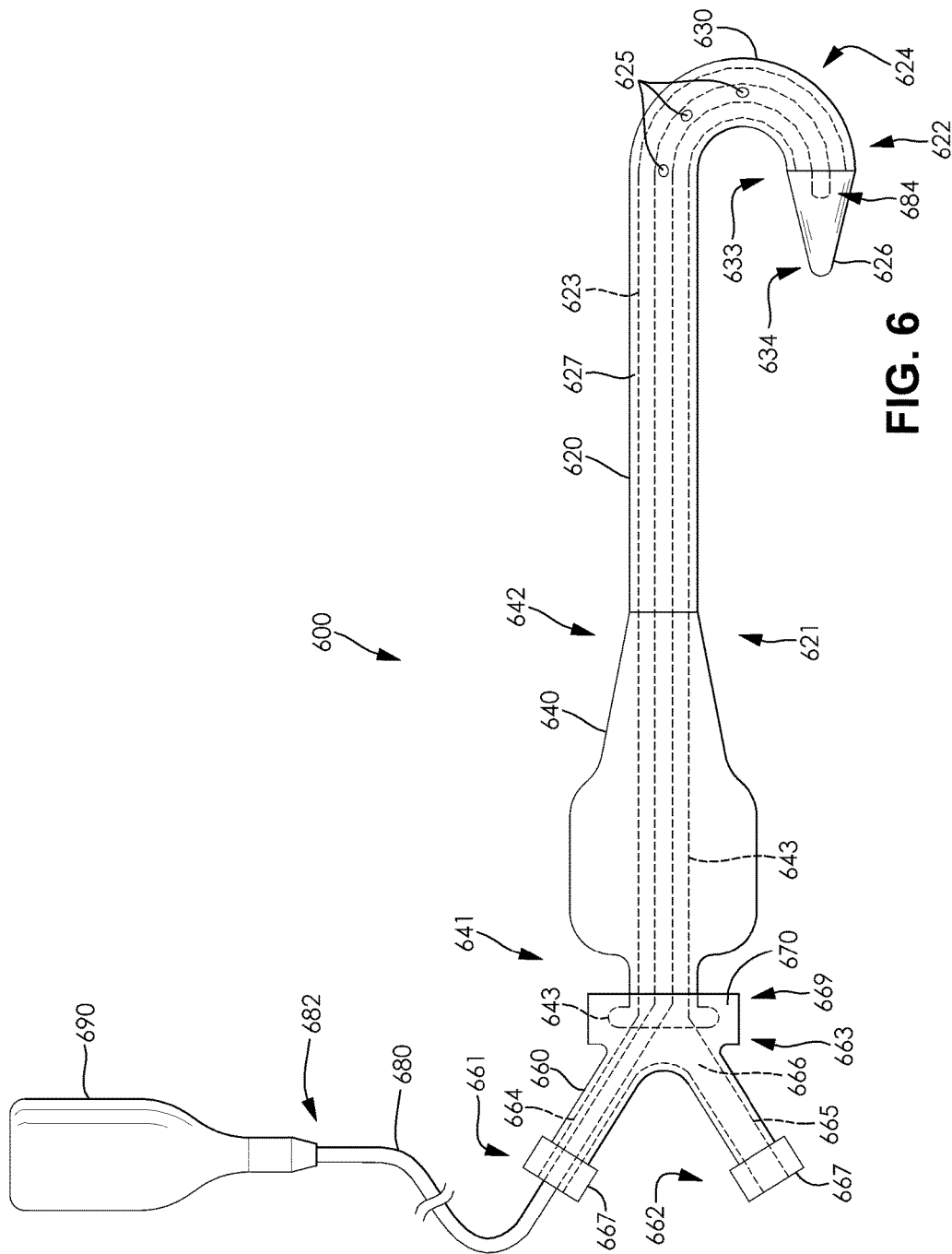
FIG. 6 is a side view of another exemplary light emitting irrigation device.

The elongate tubular member 120 has a lengthwise axis and comprises proximal 122 and distal 124 ends, and a circumferential wall 125. The circumferential wall 125 defines a plurality of apertures 130 and a lumen 126 which extends between openings at the proximal end 122 and the distal end 124. The elongate tubular member 120 is formed of a rigid material and defines a curve 128 and includes and a soft distal tip 132. The curve 128 is disposed along the lengthwise axis of the elongate tubular member 120, comprises an apex 129, and is angled to provide advantageous positioning of the distal end 124 of the elongate tubular member 120 in bodily passages, such as sinus cavities. The elongate tubular member 120 can define a curve 128 which has any angle considered suitable for a particular application, or can define a suitable number of loops (e.g., one, two, three, four, and any other number considered suitable for a particular application). Examples of angles considered suitable include angles in the range from about 1° to 360°. An exemplary light emitting irrigation device that includes a 180° curve is illustrated in FIG. 6.

While the elongate tubular member 120 has been described as having an opening at its distal end 124, the opening can be omitted and the distal end 124 can be sealed with a clear material which is attached to the distal end 124 of the elongate tubular member 120. The clear material can be formed of a soft, or semi-rigid material, and can comprise any suitable transparency.

The elongate tubular member 120 can include one or more markers (not shown) to indicate the length of the elongate tubular member 120 disposed within a bodily passage when in use. For example, one or more markers, relating to any form of measurement, can be embedded within, or disposed on the interior or exterior surface of the elongate tubular member 120.

While the elongate tubular member 120 has been described as formed of a rigid material and defining a single curve, the elongate tubular member 120 can be formed of a malleable material which allows for the user to bend the elongate tubular member 120 before or during a procedure. For example, the entirety, or segments of, the elongate tubular member 120, such as near and/or at the curve 128, can vary in stiffness and flexibility. In addition, the elongate tubular member 120 can include portions formed of a braided material which allows for torqueability of the elongate tubular member 120 during use to provide irrigation to varying portions of a treatment site. For example, the elongate tubular member 120 can include a braided portion from the proximal end 122 to the curve 128, or from the proximal end 122 to a location proximal to the apertures 130. Skilled artisans will be able to select appropriate materials for the elongate tubular member 120, and an appropriate number of, and angle for, the curve(s), according to a particular embodiment based on various considerations, including the intended use of the light emitting irrigation device, the location of the bodily passage being identified and/or treated, and the location of the curve and/or apertures.

The elongate tubular member 120 can have any suitable length, and skilled artisans will be able to select an appropriate length for inclusion in a light emitting irrigation device according to a particular embodiment based on various considerations, including the intended use of the irrigation device, and the location of the bodily passage being identified and/or treated, among others. Examples of suitable lengths for the elongate tubular member 120 include lengths in the range from about 1 cm to 20 cm. Additional exemplary lengths for the elongate tubular member include lengths in the range from about 12 cm through 15 cm.

The plurality of apertures 130 are disposed between the apex 129 of the curve 128 and the distal end 124 of the elongate tubular member 120, extend through the circumferential wall 125 of the elongate tubular member 120, and provide access to the lumen 126. The plurality of apertures 130 assist in irrigating bodily passages. For example, the plurality of apertures 130 assist with flushing bodily passages by discharging a treatment material radially from the elongate tubular member 120.

The plurality of apertures 130 can be disposed in various configurations on the elongate tubular member 120. For example, the plurality of apertures 130 can be disposed circumferentially, linearly, and/or staggered on the circumferential wall 125. In a further example, at least three apertures of the plurality of apertures 130 can be disposed circumferentially about the elongate tubular member 120, disposed on the circumferential wall 125 in a linear configuration, and/or disposed on the circumferential wall 125 in a staggered configuration. In addition, at least two of the plurality of apertures 130 can vary in diameter to assist in providing even aspiration and/or distribution of treatment material to bodily passages.

While a plurality of apertures 130 have been described and illustrated as located between the apex 129 of the curve 128 and the distal end 124 of the elongate tubular member 120, any suitable location and number of apertures can be included, and skilled artisans will be able to select an appropriate number of apertures and a suitable location on the elongate tubular member for inclusion in a light emitting irrigation device according to a particular embodiment based on various considerations, including the intended use of the light emitting irrigation device, and the location of the bodily passage being identified and/or treated. Examples of suitable numbers of apertures include one, two, three, four, five, six, seven, eight, nine, ten and any number determined suitable for a particular application. Examples of suitable locations for the plurality of apertures 130 include locations where at least one aperture of the plurality of apertures 130 is defined by the circumferential wall 125 at a point between the curve 128 (e.g., apex 129) and the distal end 124 of the elongate tubular member 120, at a point within the curve 128, or at a point between the curve (e.g., apex 129) and the proximal end 122 of the elongate tubular member 120. Alternatively, the apertures 130 can be omitted from the light emitting irrigation device 100.

The distal end 124 of the elongate tubular member 120 includes a soft distal tip 132 (e.g., an atraumatic tip) that is formed of a flexible material which can be translucent, or have partial to no transparency. While, the soft distal tip 132 is illustrated as not including any apertures 130, the soft distal tip 132 can define one or more apertures 130 which extend through the wall of the soft distal tip 132 providing access to lumen 126. The soft distal tip 132 can be attached with the distal end 124 of the elongate tubular member using various methods, and skilled artisans will be able to select an appropriate method for attaching the soft distal tip 132 to the elongate tubular member 120 according to various considerations, including the intended use of the light emitting irrigation device, and the location of the treatment site, among others. Examples of suitable methods for attaching the soft distal tip 132 to the elongate tubular member 120 include heat bonding, adhesively affixing, using threaded components, and the like. For example, the soft distal tip 132 can be formed of the same, or different, material as the elongate tubular member 120 and disposed over a portion of the elongate tubular member 120, or attached to the distal end 124 of the elongate tubular member 120. In an additional example, the distal end 124 of the elongate tubular member 120 can be cut at an angle and the proximal end of the soft distal tip 132 can be cut at angle which mirrors the cut in the elongate tubular member 120. The soft distal tip 132 can then be attached to the elongate tubular member along the mirror surfaces.

The soft distal tip 132 can be configured in any manner considered suitable for a particular application. For example, the soft distal tip 132 can be configured as tapered, rounded, or squared, and skilled artisans will be able to select an appropriate configuration based on various considerations, including the intended use of the light emitting irrigation device, and others. While the soft distal tip 132 has been described as formed of a flexible material, the soft distal tip 132 can be formed of any suitable material, and skilled artisans will be able to select an appropriate material according to a particular embodiment based on various considerations, including the intended use of the light emitting irrigation device, and the location of the bodily passage being identified and/or treated, among other considerations. Alternatively, the light emitting irrigation device 100 can omit the inclusion of the soft distal tip 132 and the distal end 124 can be formed of a soft, or semi-rigid material.

The adapter 140 comprises first 142 and second 144 proximal ends, a distal end 146 and defines first 148 and second 150 lumens. The distal end 146 of the adapter 140 is rotatably connected to the proximal end 122 of the elongate tubular member 120. The adapter 140 can be, however, otherwise attached to the elongate tubular member 120. The first lumen 148 extends between the first proximal end 142 and the first distal end 146 and is in communication with the lumen 126 of the elongate tubular member 120. The second lumen 150 extends between the second proximal end 144 and the first lumen 148 and is in communication with the first lumen 148. The first 142 and second 144 proximal ends include a connector 152 for releasably or fixedly connecting one or more elements and/or devices. The connectors 152 can include a sealing member 153 to prevent fluid from flowing out of lumens 148 and 150 and/or provide a seal around any element and/or device traversing the first 142 and/or second 144 proximal ends. For example, the sealing member 153 can comprise a one-way valve which prevents the back flow of materials. Skilled artisans will be able to select a suitable connector 152 for each of the ends of the adapter 140 according to a particular embodiment based on various considerations, including the intended use of the light emitting irrigation device, and the devices being used in combination with the light emitting irrigation device.

An exemplary structure for rotatably connecting the elongate tubular member 120 and the adapter 140 is shown at 143. The elongate tubular member 120 has a proximal end 122 that defines a projection 123 that is received by a socket 147 defined by the distal end 146 of the adapter 140. The projection 123 and socket 147 advantageously fit together in a manner that permits rotation of the elongate tubular member 120 relative to the adapter 140 but does not permit axial disconnection of these elements. The connection advantageously includes a degree of play between the elements to facilitate navigation of the elongate tubular member 120 to a point of treatment. While the rotatable component has been described and illustrated at 143, and as having a degree of play, the light emitting irrigation device can include a rotatable component at other suitable locations along the length of the elongate tubular member 120, and include various degrees of play, and skilled artisans will be able to select a suitable location for the rotatable connection and the extent of play incorporated into any particular light emitting irrigation device 100 according to a particular embodiment based on various considerations, including the intended use of the device, and the location of the bodily passage being identified and/or treated. Examples of suitable positions for the rotatable component include positions located between the proximal end 122 of the elongate tubular member 120 and the proximal end of the soft distal tip 132.

While the adapter 140 has been illustrated as having a bifurcated configuration, the adapter can include any suitable number of branches, and skilled artisans will be able to select an appropriate number of branches for inclusion in a light emitting irrigation device according to a particular embodiment based on various considerations, including the number of lumens defined by the elongate tubular member, and the number of devices attached to and/or traversing the adapter, among others. Examples of suitable numbers of branches include one, two, three, four and any number determined suitable for a particular application. For example, the adapter can comprise a single shaft defining one or more lumens in communication with one another or separate from one another.

Any suitable material can be used to form the elongate tubular member 120, soft distal tip 132, the adapter 140, and the connectors 152, and skilled artisans will be able to select appropriate materials for inclusion in a light emitting irrigation device according to a particular embodiment based on various considerations, including the intended use of the light emitting irrigation device, and the location of the bodily passage being identified and/or treated. Examples of materials considered suitable include plastics, biocompatible materials, metals, and other materials used in the manufacture of conventional catheters, sheaths, connectors, adapters, and the like.

The optical fiber 160 extends between proximal 162 and distal 164 ends and defines a light path extending through its length which allows axially-directed light to emanate from the distal end 164 of the optical fiber 160. The optical fiber 160 extends through the first lumen 148 of the adapter 140 and is disposed within the lumen 126 of the elongate tubular member 120. The proximal end 162 of the optical fiber 160 is adapted to be operatively connected or attached to the light source 180. The distal end 164 of the optical fiber 160 is attached to the circumferential wall 125 of the elongate tubular member 120 at a point between the plurality of apertures 130 and the distal end 124 relative to the lengthwise axis. The optical fiber 160 can be, however, attached along its entire length, or at multiple locations along its length, to the circumferential wall 125. For example, the optical fiber 160 can be attached to the circumferential wall 125 between at least two of the plurality of apertures 130, within the curve 128, and/or proximal to the curve 128.

Attaching the optical fiber 160 to the elongate tubular member 120 can be accomplished using various methods and materials. For example, attaching the optical fiber 160 to the circumferential wall 125 can be accomplished by inserting the optical fiber 160 past the distal end 124 of the elongate tubular member 120, attaching the optical fiber 160 to the circumferential wall 125, and cutting the optical fiber 160 flush with the elongate tubular member 120. Skilled artisans will be able to select appropriate methods and materials for attaching the optical fiber 160 to the circumferential wall 125 of the elongate tubular member 120 according to a particular embodiment based on various considerations, including the intended use of the light emitting irrigation device, and the desired length of the elongate tubular member and/or optical fiber. Examples of other suitable methods for attaching the optical fiber 160 to the elongate tubular member 120 include using adhesive, heat fusing, and other methods considered suitable. For example, the optical fiber can be attached to the elongate tubular member 120 by heating a portion of the circumferential wall 125 with a heated building wire and attaching the optical fiber 160 to the heated portion of the circumferential wall 125.

The configuration of lumen 148 of the adapter 140 can be altered subsequent to the attachment of the optical fiber 160 to the circumferential wall 125 of the elongate tubular member 120 to prevent material from flowing out of proximal end 142 of the adapter 140. For example, the portion of the lumen 148 from the proximal end 142 to the converging point of lumen 148 and lumen 150 can be tapered from the proximal end 142 to the converging point. Alternatively, lumen 148 can include multiple sealing members and/or be filled with material from the proximal end 142 to the converging point to prevent the back flow of materials.

While only the distal end 164 of the optical fiber 160 has been described as emitting light generated by the light source 180, the optical fiber 160 and elongate tubular member 120 can be adapted to emit light radially from the light emitting irrigation device 100. For example, the radially-directed light can be emitted through the plurality of apertures 132 allowing a user to transcutaneously visualize the position of the plurality of apertures 132 at the treatment site. In addition, while the optical fiber 160 has been illustrated as extending through the first lumen 148 of the adapter 140, the optical fiber 160 can alternatively extend through the second lumen 150 of the adapter 140.

Any suitable optical fiber 160 can be used in the light emitting irrigation devices described herein. Commercially available optical fibers considered suitable for use in the devices described herein include plastic optical fibers and glass optical fibers, with or without cladding. The optical fiber 160 can have any suitable length, and skilled artisans will be able to select an appropriate length for inclusion in a light emitting irrigation device according to a particular embodiment based on various considerations, including the intended use of the irrigation device, and the location of the bodily passage intended to be identified and/or treated. For example, alternative to a flush configuration as described above, the optical fiber 160 can have a length that allows for a portion of the optical fiber 160 to extend beyond, or proximal to, the distal end 124 of the elongate tubular member 120 and/or a length that allows a portion of the optical fiber 160 to extend beyond the proximal end 122 of the elongate tubular member 120 and/or the proximal end 142 of the adapter 140 to the light source 180. When the optical fiber 160 extends beyond the proximal end 122 of the elongate tubular member 120 and/or the proximal end 142 of the adapter 140, an extension sheath (not shown) can be disposed over the optical fiber 160 from the proximal end 122 of the elongate tubular member 120 and/or the proximal end 142 of the adapter 140 to the light source 180.

The lumen 126 of the elongate tubular member 120 is configured to have a diameter that allows the optical fiber 160 to extend through a portion, or the entirety, of its length while also providing sufficient irrigation capabilities. Examples of suitable diameters for lumen 126 include diameters in the range from about 0.010 inch to about 0.25 inch. An exemplary elongate tubular member 120 includes a lumen 126 with a diameter in the range from about 0.020 inch to about 0.050 inch. An additional exemplary elongate tubular member 120 includes a lumen 126 with a diameter of about 0.038 inch.

The effectiveness of the light emitting irrigation device 100 can be altered based on the size of the lumen 126 and apertures 130, and skilled artisans will be able to select appropriate dimensions for the lumen 126 and the apertures 130 according to a particular embodiment based on various considerations, including the intended use of the light emitting irrigation device, and the size and/or location of the bodily passage to be identified and/or treated.

The light source 180 is operatively connected or attached to the proximal end 162 of the optical fiber 160 and includes a fiber coupling 182 which provides communication between the light source 180 and the optical fiber 160. Light generated by the light source 180 travels through the light path defined by the optical fiber 160 and is emitted axially from the distal end 164 of the optical fiber 160. Alternatively, the proximal end 122 of the elongate tubular member 120, or a proximal end 142 or 144 of the adapter 140, can include one or more connectors for attaching the light source 180. While the light source 180 has been described and illustrated as attached to the proximal end 162 of the optical fiber 160, the light source 180 can, alternatively, be omitted from the irrigation device and provided separately.

Any suitable light source 180 can be used with the light emitting irrigation device 100. Commercially-available light sources considered suitable for use with the light emitting irrigation device 100 include xenon, laser, LED, halogen, and other suitable light sources. While particular light sources have been described, skilled artisans will be able to select an appropriate light source for inclusion in a light emitting irrigation device according to a particular embodiment based on various considerations, including the location of the bodily passage being identified and/or treated, among others.

It is noted that, while a single optical fiber 160 is described and illustrated in the figures, two or more different optical fibers can be used to independently provide axially-directed and/or radially directed light. The two optical fibers can extend through lumen 126 defined by the wall 125 of the elongate tubular member 120 and can be operatively connected or attached to the same or two different light sources. In addition, the light source can include one or more switches to allow a user to selectively turn on and off, or dim, a selected optical fiber.

When using the light emitting irrigation device 100, a user is able to identify the placement of the elongate tubular member 120 within a bodily passage by activating the light source 180 and locating the axially and/or radially-directed light emitting from the optical fiber 160. In addition, by visualizing the axially and/or radially-directed light, the user can identify the portion of the bodily passage that will be subject to the irrigation procedure. Once the treatment site has been identified and located, the user can irrigate the bodily passage. For example, a user can flush a treatment site by injecting treatment material through the lumen 126 of the elongate tubular member 120, forcing the treatment material to exit through the plurality of apertures 130 and/or the opening at the distal end 124 of the elongate tubular member 120.

Figure 2:
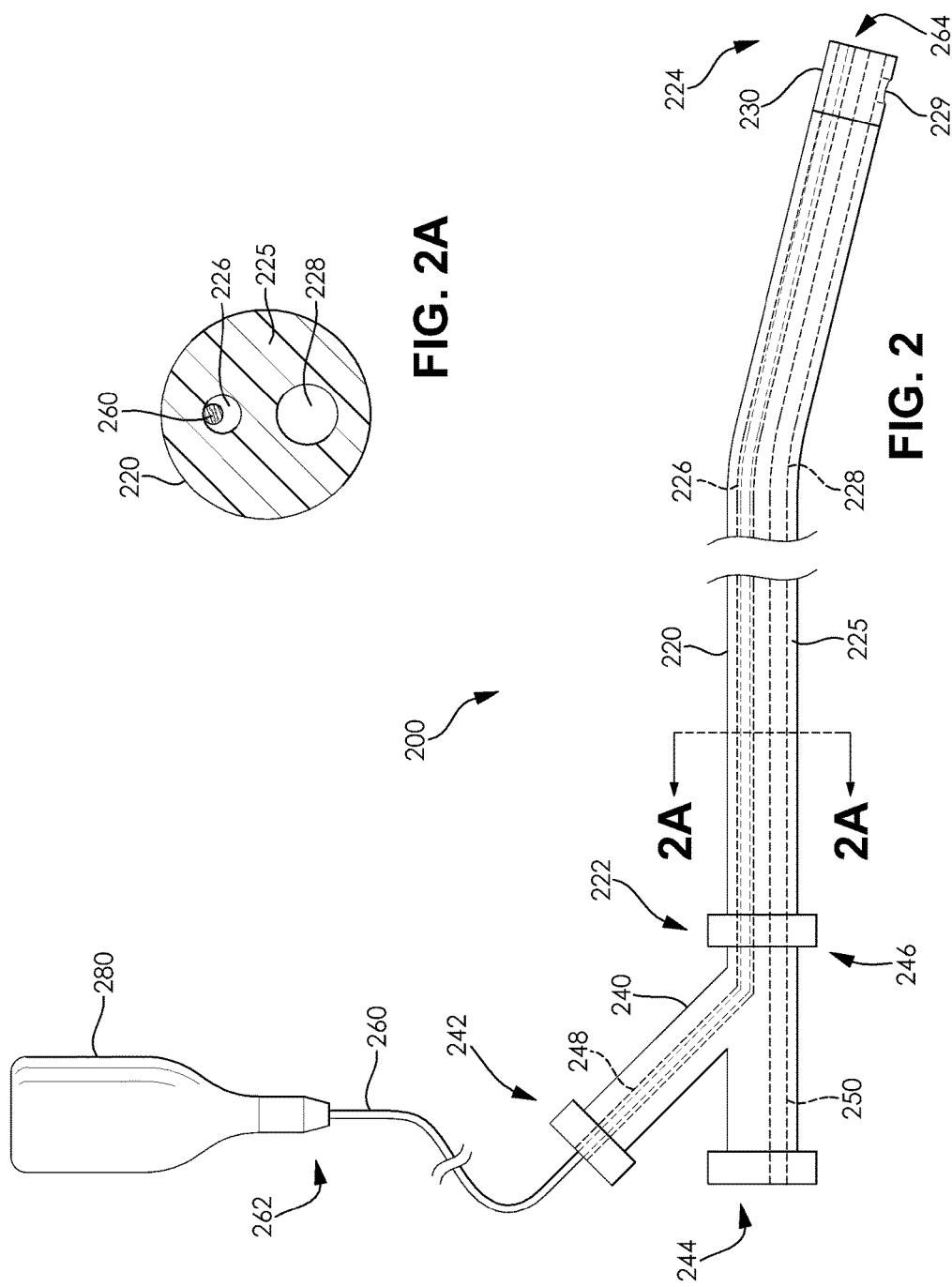
FIG. 2 is a side view of another exemplary light emitting irrigation device.

FIGS. 2 and 2A illustrate another exemplary light emitting irrigation device 200. The light emitting irrigation device 200 illustrated in FIGS. 2 and 2A is similar to the exemplary light emitting irrigation device 100 illustrated in FIGS. 1 and 1A, except as detailed below. The light emitting irrigation device 200 comprises an elongate tubular member 220, an adapter 240, an optical fiber 260, and a light source 280. The elongate tubular member 220 has a lengthwise axis and comprises proximal 222 and distal 224 ends, and a wall 225 and defines first 226 and second 228 lumens extending from openings located at the proximal 222 and distal 224 ends.

The first lumen 226 is not in communication with the second lumen 228 and is disposed substantially parallel to the second lumen 228. However, while the first lumen 226 has been described as being disposed substantially parallel to the second lumen 228, the elongate tubular member 220 can include various other lumen configurations, and skilled artisans will be able to select an appropriate configuration according to a particular embodiment based on various considerations, including the intended use of the irrigation device, and the location of the treatment site, among others. Examples of suitable configurations include first and second lumens that are disposed at an angle with respect to one another, and/or first and second lumens that wrap around one another.

A soft distal tip 230 can be attached to the distal end 224 of the elongate tubular member 220 and has a wall which defines an aperture 229. However, while a single aperture 229 has been illustrated and described as defined by the wall of the soft distal tip 230, the wall of the soft distal tip 230 and/or the elongate tubular member 220 can define one or more apertures, or the soft distal tip 230 and/or elongate tubular member 220 can omit the inclusion of one or more apertures, and skilled artisans will be able to select an appropriate number of apertures according to a particular embodiment based on various considerations, including the intended use of the light emitting irrigation device, and the location of the bodily passage being identified and/or treated.

The soft distal tip 230 can be attached in a variety of manners, as described above. For example, the soft distal tip can include two lumens and have a proximal end cut at an angle which mirrors a cut on the distal end 224 of the elongate tubular member 220. The soft distal tip 230 can then be attached to the distal end 224 of the elongate tubular member 220. In a further example, the soft distal tip 230 can comprise two pieces of material, each of which includes a lumen, cut at an angle to match cuts made at the distal end 224 of the elongate tubular member 220 with respect to each lumen 226 and 228. Each piece of the soft distal tip 230 can be attached to the distal end 224 of the elongate tubular member so that the lumens of each piece of the soft distal tip 230 are in communication with lumen 226 or 228 of the elongate tubular member 220. In a further example, another piece of material could cover the two pieces of the soft distal tip 230 to provide a uniform structure at the distal end 224 of the elongate tubular member 220.

The adapter 240 comprises first 242 and second 244 proximal ends, a distal end 246 and defines first 248 and second 250 lumens. The adapter 240 is attached to the proximal end 222 of the elongate tubular member 220. The adapter 340 can be, however, rotatably connected to the elongate tubular member 320. The first lumen 248 extends between openings located on the first proximal end 242 and the first distal end 246 and is in communication with the first lumen 226 of the elongate tubular member 220. The second lumen 250 extends between openings located on the second proximal end 244 and the first distal end 246 and is in communication with the second lumen 228 of the elongate tubular member 220.

The optical fiber 260 extends between proximal 262 and distal 264 ends and defines a light path extending through its length. The optical fiber 260 extends through the first lumen 248 of the adapter 240 and is disposed within first lumen 226 of the elongate tubular member 220. The proximal end 262 of the optical fiber 260 is adapted to be operatively connected or attached to the light source 280. The distal end 264 of the optical fiber 260 is attached to the wall 225 of the elongate tubular member 220. Attaching the optical fiber 260 to the elongate tubular member 220 can be accomplished using any suitable method, including those described above with respect to FIG. 1. Alternatively, the optical fiber 260 can be attached to the wall 225 of the elongate tubular member 220 by cutting a window from a portion of the elongate tubular member 220 and adhesively affixing, or otherwise attaching, a portion of the optical fiber 260 to a portion of the elongate tubular member 220.

While the optical fiber 260 has been described and illustrated as extending through the first lumen 248 of the adapter 240 and being disposed within first lumen 226 of the elongate tubular member 220, the optical fiber 260 can alternatively extend through the second lumen 250 of the adapter 240 and be disposed within the second lumen 228 of the elongate tubular member 220.

The light source 280 is operatively connected or attached to the proximal end 262 of the optical fiber 260 such that light generated by the light source 280 is able to travel through the light path defined by the optical fiber 260. While the light source 280 has been described and illustrated as attached to the proximal end 262 of the optical fiber 260, the light source 280 can, alternatively, be omitted from the irrigation device and provided separately.

It is noted that, while a single optical fiber 260 is described and illustrated in the figures, two or more different optical fibers can be used to independently provide axially-directed and/or radially directed light. The two optical fibers can be disposed within the same or different lumens defined by the wall 225 of the elongate tubular member 120 and can be operatively connected or attached to the same or two different light sources. In addition, one or more switches can be provided to allow a user to selectively turn on and off, or dim, a selected optical fiber.

Figure 3:
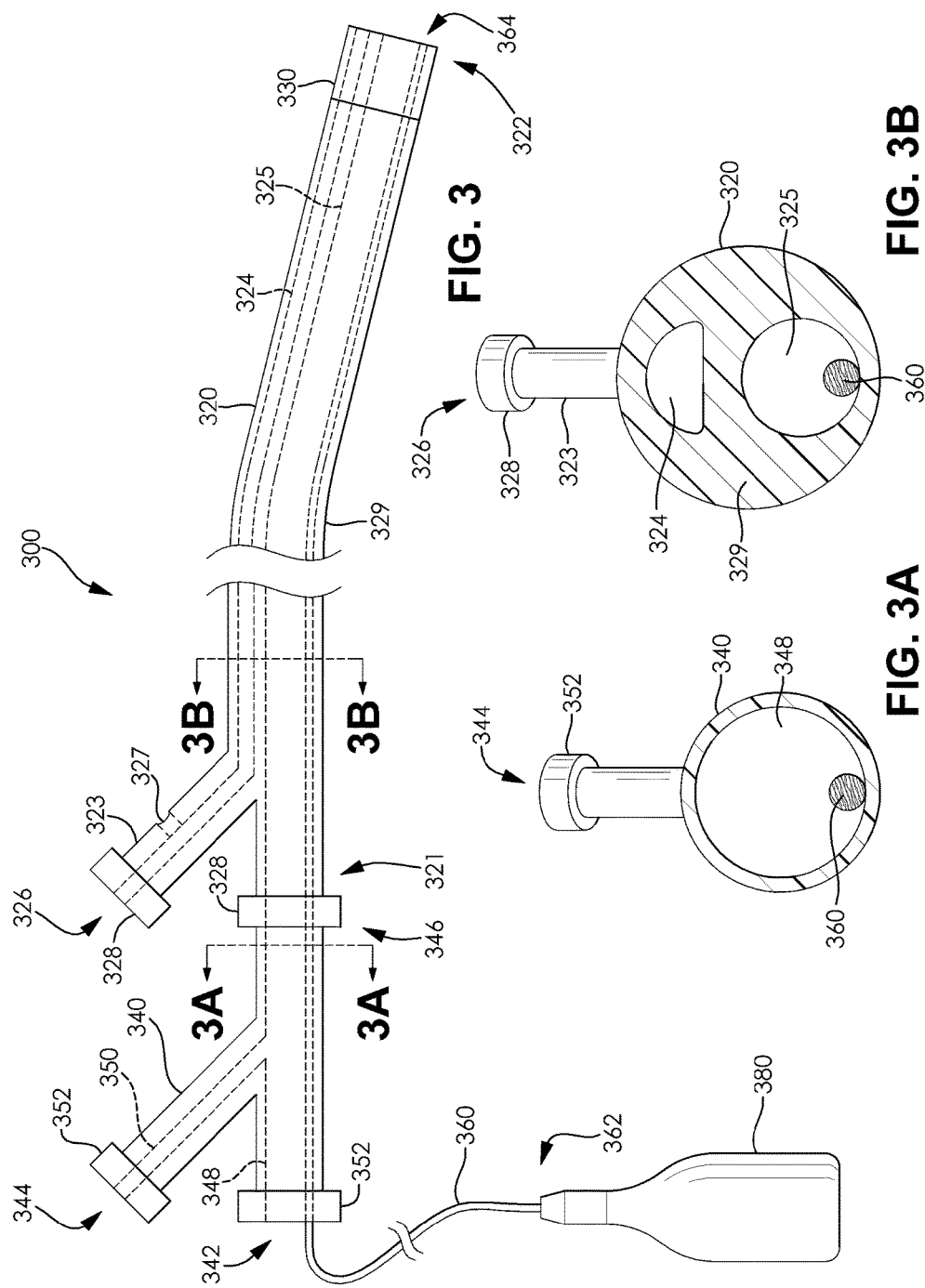
FIG. 3 is a side view of another exemplary light emitting irrigation device.

FIGS. 3, 3A, and 3B illustrate another exemplary light emitting irrigation device 300. The light emitting irrigation device 300 illustrated in FIGS. 3, 3A, and 3B is similar to the exemplary light emitting irrigation device 200 illustrated in FIGS. 2 and 2A, except as detailed below.

The light emitting irrigation device 300 comprises an elongate tubular member 320, an adapter 340, an optical fiber 360, and a light source 380. The elongate tubular member 320 has a lengthwise axis and comprises proximal 321 and distal 322 ends, an irrigation port 323, and a wall 329 which defines first 324 and second 325 lumens. The irrigation port 323 branches off of the elongate tubular member 320 distal to the proximal end 321, has a proximal end 326, and defines an aperture 327 and a portion of the first lumen 324. The aperture 327 extends through the wall of the irrigation port 323 and provides access to the lumen 324. The first lumen 324 extends from openings located at the proximal end 326 and distal end 322 of the elongate tubular member 320. The second lumen 325 extends between openings located at the proximal end 321 and distal 322 end of the elongate tubular member 320. The proximal end 321 of the elongate tubular member 320 and the proximal end 326 of the irrigation port 323 include connectors 328 for releasably or fixedly connecting one or more elements and/or devices.

While the first lumen 324 is shown as having a semi-circular configuration, each of the lumens described herein can be configured in any suitable manner, and skilled artisans will be able to select a suitable configuration for a lumen for inclusion in a light emitting irrigation device according to a particular embodiment based on various considerations, including the intended use of the light emitting irrigation device, and the type of treatment being provided to a bodily passage. Examples of suitable lumen configurations which can be defined by the wall of the elongate tubular members described herein include, but are not limited to, circular, semi-circular, triangular, square, rectangular, pentagonal, hexagonal, heptagonal, octagonal, and any other configuration considered suitable for a particular application.

The second lumen 325 is not in communication with the first lumen 324 and is disposed substantially parallel to the first lumen 324. However, while the second lumen 325 has been described as being disposed substantially parallel to the first lumen 324, various other configurations can be used, and skilled artisans will be able to select an appropriate configuration according to a particular embodiment based on various considerations, including the intended use of the irrigation device, and the location of the treatment site, among others. Examples of suitable configurations include first and second lumens that are disposed at an angle with respect to one another, and/or first and second lumens that wrap around one another.

The adapter 340 comprises first 342 and second 344 proximal ends, a distal end 346 and defines first 348 and second 350 lumens. The adapter 340 is attached to the proximal end 321 of the elongate tubular member 320. The adapter 340 can be, however, rotatably connected to the elongate tubular member 320. The first lumen 348 extends between openings located at the first proximal end 342 and the first distal end 346 and is in communication with the second lumen 325 of the elongate tubular member 320. The second lumen 350 extends between openings located at the second proximal end 344 and the first lumen 348 and is in communication with the first lumen 348. The first 342 and second 344 proximal ends include a connector 352 for releasably or fixedly connecting one or more elements and/or devices. The connectors 328 and/or 352 can include a sealing member to prevent fluid from flowing out of lumens 324, 325, 348, and 350 and/or provide a seal around any element and/or device traversing these elements.

While a single irrigation port 323 and an adapter 340 having a bifurcated configuration have been illustrated and described, the light emitting irrigation device 300 can include any suitable number of irrigation ports and/or adapters with any suitable number of branches, and skilled artisans will be able to select an appropriate number of irrigation ports and branches for inclusion in a light emitting irrigation device according to a particular embodiment based on various considerations, including the number of lumens defined by the elongate tubular member, and the intended use of the light emitting irrigation device. Examples of suitable numbers of irrigation ports and branches include one, two, three, four and any number determined suitable for a particular application.

The optical fiber 360 extends between proximal 362 and distal 364 ends and defines a light path extending through its length. The optical fiber 360 extends through the first lumen 348 of the adapter 340 and is disposed within the second lumen 325 of the elongate tubular member 320. The proximal end 362 of the optical fiber 360 is adapted to be operatively connected or attached to the light source 380.

While the optical fiber 360 has been described and illustrated as extending through the first lumen 348 of the adapter 340 and being disposed in the second lumen 325 of the elongate tubular member 320, the optical fiber 360 can alternatively extend through the second lumen 350 of the adapter 340 and be disposed within the second lumen 325 of the elongate tubular member 320.

In use, the configuration of the light emitting device 300 advantageously allows for a user to simultaneously provide suctioning and flushing at a treatment site. For example, the proximal end 326 of the irrigation port 323 and/or connector 328 can be adapted to receive and/or attach a portion of a suctioning device, while the second proximal end 344 of the adapter 340 and/or connector 352 can be adapted to receive and/or attach a portion of an infusion device, or vice versa. When suction is being applied through the irrigation port 323, the aperture 327 of the irrigation port 323 advantageously allows for the user to increase or decrease the amount of suction being applied to a treatment site.

While the elongate tubular member 320 has been described and illustrated as not including an aperture(s), the wall 329 of the elongate tubular member 320 and/or an attached soft distal tip 330 can define one or more apertures, and skilled artisans will be able to select an appropriate number of apertures according to a particular embodiment based on various considerations, including the intended use of the light emitting irrigation device, and the location of the bodily passage being identified and/or treated.

Figure 4:
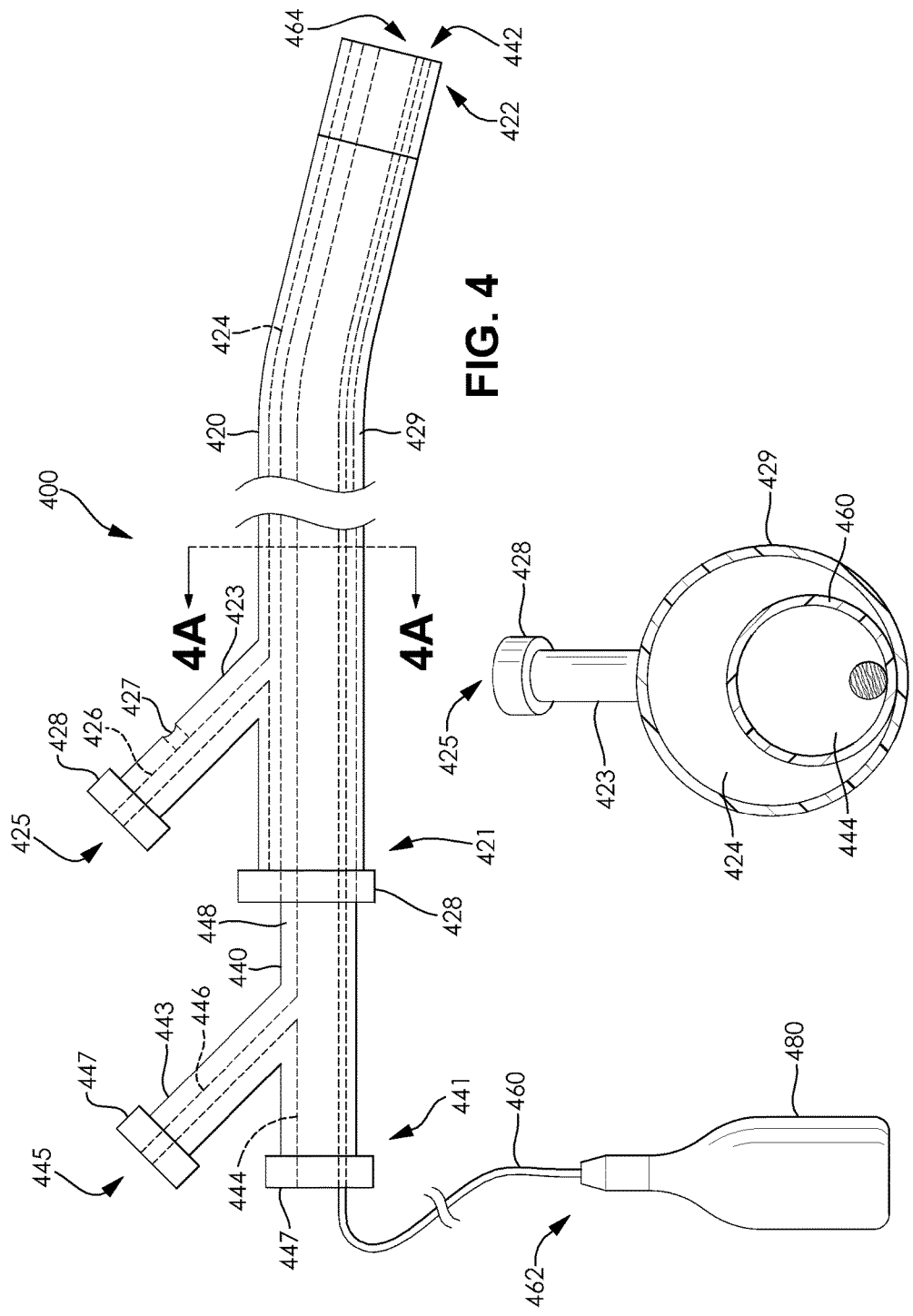
FIG. 4 is a side view of another exemplary light emitting irrigation device.

FIGS. 4 and 4A illustrate another exemplary light emitting irrigation device 400. The light emitting irrigation device 400 illustrated in FIGS. 4 and 4A is similar to the exemplary light emitting irrigation device 100 illustrated in FIGS. 3 and 3A, except as detailed below.

The light emitting irrigation device 400 comprises a first elongate tubular member 420, a second elongate tubular member 440, an optical fiber 460, and a light source 480. The first elongate tubular member 420 has a lengthwise axis and comprises proximal 421 and distal 422 ends, an irrigation port 423, and a circumferential wall 429. The circumferential wall 429 defines a lumen 424 extending from openings located at the proximal 421 and distal 422 ends. The irrigation port 423 branches off of the first elongate tubular member 420 distal to the proximal end 421, has a proximal end 425, and defines a lumen 426 and an aperture 427. The lumen 426 of the irrigation port 423 extends from an opening located at the proximal end 425 of the irrigation port 423 and is in communication with lumen 424 of the elongate tubular member 420. The aperture 427 extends through the wall of the irrigation port 423 and provides access to lumen 426. The proximal end 421 of the first elongate tubular member 420 and the proximal end 425 of the irrigation port 423 include connectors 428 which allow for releasably or fixedly connecting one or more elements and/or devices.

The second elongate tubular member 440 has a lengthwise axis and comprises proximal 441 and distal 442, a second irrigation port 443, and a wall 448. The wall 448 defines a lumen 444 which extends between openings located at the proximal 441 and distal 442 ends. The second irrigation port 443 branches off of the second elongate tubular member 440 distal to the proximal end 441, has a proximal end 445, and defines a lumen 446. The lumen 446 of the second irrigation port 443 extends from an opening located at the proximal end 445 of the second irrigation port 443 and is in communication with lumen 444. The proximal end 441 of the second elongate tubular member 440 and the proximal end 445 of the second irrigation port 443 include connectors 447 which allow for releasably or fixedly connecting one or more elements and/or devices. The connectors 428 and/or 447 can include a sealing member to prevent fluid from flowing out of lumens 424, 426, 444, and 446 and/or provide a seal around any element and/or device traversing these elements. The second elongate tubular member 440 extends through the proximal end 421 of the first elongate tubular member 420 and is attach at connector 428. The distal end 442 of the second elongate tubular member 440 is disposed flush with the distal end 422 of the first elongate tubular member 420. The distal end 442 of the second elongate tubular member can be, however, disposed proximal or distal to the distal end 422 of the first elongate tubular member 420. The lumen 444 of the second elongate tubular member 440 is not in communication with the lumen 426 of the first elongate tubular member 420.

While each elongate tubular member 420 and 440 includes a single irrigation port, the light emitting irrigation device 400 can include any suitable number of irrigation ports, and skilled artisans will be able to select an appropriate number of irrigation ports according to a particular embodiment based on various considerations, including the intended use of the light emitting irrigation device, and the location of the treatment site. Examples of suitable numbers of irrigation ports include one, two, three, four and any number determined suitable for a particular application.

The optical fiber 460 extends between proximal 462 and distal 464 ends and defines a light path extending through its length. The proximal end 462 of the optical fiber 460 is adapted to be operatively connected or attached to the light source 480 and its distal end 464 is disposed within the lumen 444 of the second elongate tubular member 440. While the optical fiber 460 has been illustrated as extending through the proximal end 441 of the second elongate tubular member 440, the optical fiber 460 can alternatively extend through the second irrigation port 443 of the second elongate tubular member 440.

In use, the configuration of the light emitting irrigation device 400 advantageously allows for a user to simultaneously provide suctioning and flushing at a treatment site. For example, the proximal end 425 of the irrigation port 423 and/or connector 428 can be adapted to receive and/or attach a portion of a suctioning device, while the proximal end 445 of the second irrigation port 443 and/or connector 447 can be adapted to receive and/or attach a portion of an infusion device, or vice versa. During use, the aperture 427 of the irrigation port 423 advantageously allows for the user to increase or decrease the amount of suction being applied to a treatment site.

While the elongate tubular member 420 has been described and illustrated as not including an aperture(s), the wall 429 of the elongate tubular member 420 can define one or more apertures, and skilled artisans will be able to select an appropriate number of apertures according to a particular embodiment based on various considerations, including the intended use of the light emitting irrigation device, and the location of the bodily passage being identified and/or treated.

Figure 5:
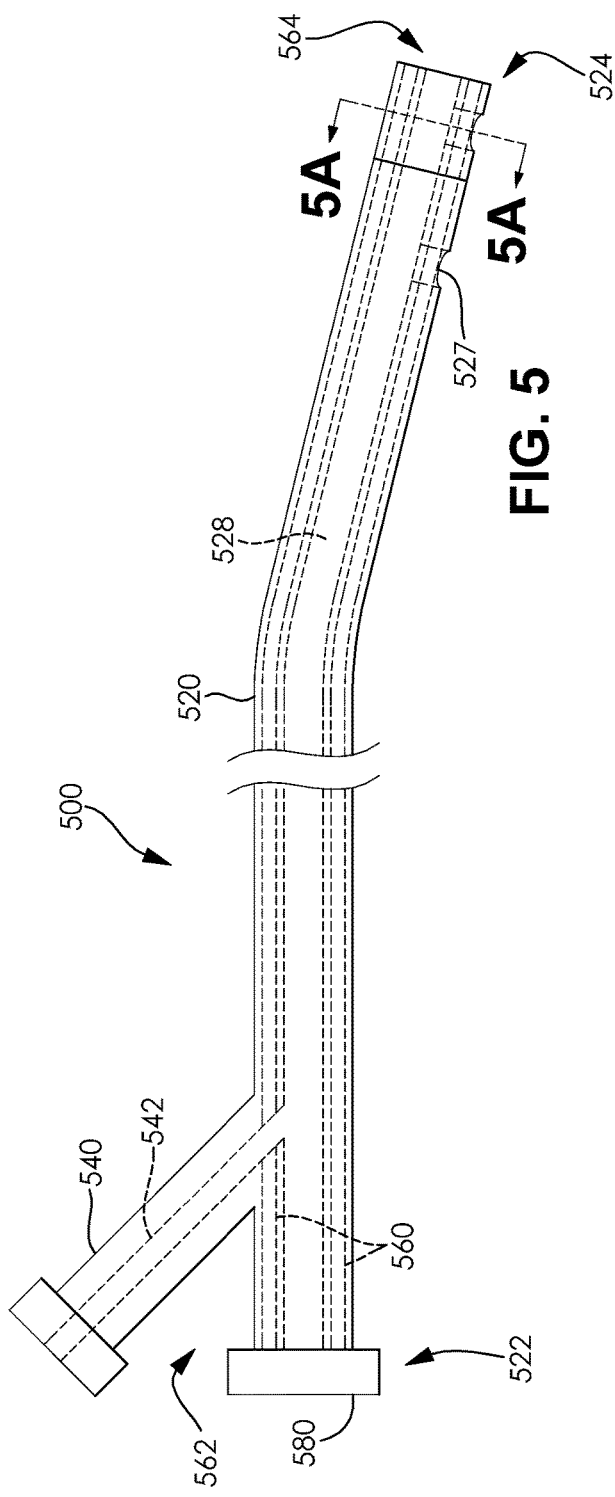
FIG. 5 is a side view of another exemplary light emitting irrigation device.
Figure 5A:
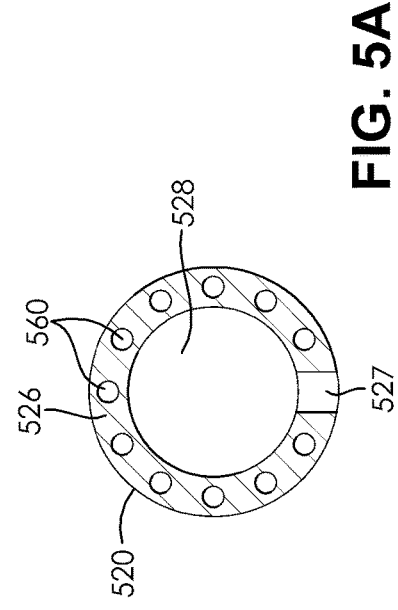
FIG. 5A is a sectional view of the light emitting irrigation device in FIG. 5, taken along line 5A-5A.

FIGS. 5 and 5A illustrate a third exemplary light emitting irrigation device 500. The irrigation device 500 illustrated in FIGS. 5 and 5A is similar to the exemplary light emitting irrigation device 100 illustrated in FIGS. 1 and 1A, except as detailed below. The irrigation device 500 comprises an elongate tubular member 520, a plurality of optical fibers 560, and a light source 580. The elongate tubular member 520 has a lengthwise axis and comprises proximal 522 and distal 524 ends, a wall 526, and an irrigation port 540. The wall 526 defines a plurality of apertures 527 and a lumen 528 that extends between openings located at the proximal end 522 and the distal end 524. The irrigation port 540 branches off of the elongate tubular member 520 distal to the proximal end 522 and defines a lumen 542 in communication with the lumen 528 of the elongate tubular member 520. The plurality of apertures 527 extend through the wall 526 of the elongate tubular member 520 and provide access to lumen 528.

While a plurality of apertures 527 have been illustrated and described, the elongate tubular member 520 can include a single aperture, or omit the inclusion of the apertures, and skilled artisans will be able to select an appropriate number of apertures according to a particular embodiment based on various considerations, including the intended use of the light emitting irrigation device, and the location of the bodily passage being identified and/or treated.

Each of the plurality of optical fibers 560 extends between proximal 562 and distal 564 ends and defines a light path extending through its length. Each of the plurality of optical fibers 560 is embedded within the wall 526 of the elongate tubular member 520 and has a proximal end 562 in communication with the light source 580 and a distal end 562 disposed flush with, proximal to, or distal to, the distal end 524 of the elongate tubular member 520. Alternatively, the proximal ends 562 of the optical fibers 560 can be gathered in a trunk and operatively connected or attached to the light source 580. While the optical fibers 560 have been described as embedded within the wall of the elongate tubular member 520, the optical fibers 560 can be disposed and attached within lumens that have been extruded within the wall 526 of the elongate tubular member 520.

The plurality of apertures 527 are illustrated as being disposed in a linear configuration and located in a position where an optical fiber 560 has been omitted from the wall 526 of the elongate tubular member 520. The plurality of apertures 527 can be, however, disposed at other various locations depending on the number and location of the optical fibers 560 included in the light emitting irrigation device 500.

The light source 580 is operatively connected or attached to the proximal end 522 of the elongate tubular member 520 such that light generated by the light source 580 is able to travel through the light path defined by each of the plurality of optical fibers 560. While the light source 580 has been described and illustrated as attached to the proximal end 522 of the elongate tubular member 520, the light source 580 can alternatively be omitted from the irrigation device and provided separately.

It is noted that the plurality of optical fibers 560 can be used to independently or in combination with one another to provide axially-directed and/or radially directed light. For example, additional apertures can be disposed along the length of the elongate tubular member in communication with one or more of the optical fibers 560 to allow radially directed light to emit from the light emitting irrigation device 500. The plurality of optical fibers 560 can be operatively connected or attached to the same or two different light sources, which can include one or more switches to allow a user to selectively turn on and off, or dim, a selected optical fiber.

FIG. 6 is a side view of another exemplary light emitting irrigation device 600. The light emitting irrigation device 600 illustrated in FIG. 6 is similar to the exemplary light emitting irrigation device 100 illustrated in FIGS. 1 and 1A, except as detailed below. The light emitting irrigation device 600 comprises an elongate tubular member 620, a fitting 640, an adapter 660, an optical fiber 680, and a light source 690.

The elongate tubular member 620 has a lengthwise axis and comprises proximal 621 and distal 622 ends, and a circumferential wall 627. The elongate tubular member defines a curve 624 having an apex 630 and includes a soft distal tip 626. The circumferential wall 627 defines a lumen 623 which extends between openings at the proximal end 621 and the distal end 622, and a plurality of apertures 625. The curve 624 is disposed along the lengthwise axis of the elongate tubular member 620 and configured at 180° to provide advantageous positioning of the distal end 624 of the elongate tubular member 620 in bodily passages, such as sinus cavities. While a 180° curve has been described and illustrated, other suitable angles can be included in a light emitting irrigation device, and skilled artisans will be able to select a suitable angle according to a particular embodiment based on various considerations, including the intended use of the light emitting irrigation device, and the size and/or location of the bodily passage be identified and/or treated.

The plurality of apertures 625 are disposed proximal to the distal end 622 of the elongate tubular member 620, extend through the wall 627 of the elongate tubular member 620, and provide access to lumen 623. Alternatively, the plurality of apertures 625 can also be disposed within the soft distal tip 626 to assist in irrigating a treatment site. Alternatively, the plurality of apertures 625 can be disposed in various other locations along the length of the elongate tubular member 620, as described above.

While a plurality of apertures 625 have been described and illustrated as located proximal to the distal end 622 of the elongate tubular member 620, any suitable location and number of apertures can be included, and skilled artisans will be able to select an appropriate number of apertures and a suitable location on the elongate tubular member for inclusion in a light emitting irrigation device according to a particular embodiment based on various considerations, including the intended use of the light emitting irrigation device, and the location of the bodily passage being identified and/or treated. Examples of suitable numbers of apertures include one, two, three, four, five, six, seven, eight, nine, ten and any number determined suitable for a particular application.

The distal end 622 of the elongate tubular member 620 includes a soft distal tip 626 (e.g., an atraumatic tip) having proximal 633 and distal 634 ends. The soft distal tip 626 is a solid member formed of a clear flexible material, and has a tapered configuration from its proximal end 633 to its distal end 634. The soft distal tip 626 can be attached with the distal end 622 of the elongate tubular member 620 in various manners. For example, the soft distal tip 626 can be rotatably attached to the elongate tubular member 620, or can be formed from the same material as the elongate tubular member 620. Attaching the soft distal tip 626 to the elongate tubular member 620 can be accomplished in various ways, and skilled artisans will be able to select an appropriate method for attaching the soft distal tip 626 to the elongate tubular member 620 according to a particular embodiment based on various considerations, including the intended use of the light emitting irrigation device, and the location of the treatment site, among others. Examples of suitable methods for attaching the soft distal tip 626 with the elongate tubular member 620 include heat bonding, adhesively affixing, using threaded components, a projection and socket, and the like.

While the soft distal tip 626 has been described as composed of a clear flexible material, the soft distal tip can be manufactured from any suitable material and have any suitable transparency, and skilled artisans will be able to select an appropriate material and transparency for the soft distal tip according to a particular embodiment based on various considerations, including the intended use of the light emitting irrigation device, and the location of the bodily passage being identified and/or treated.

The fitting 640 is attached to the proximal end 621 of the elongate tubular member 620 and has proximal 641 and distal 642 ends and defines a lumen 643 which extends between openings located at the proximal end 641 and the distal end 642. The fitting 640 can be, however, rotatably connected to the elongate tubular member 620. Alternatively, the fitting 640 can be omitted and the elongate tubular member 620 can be directly attached to the adapter 660.

The adapter 660 comprises first 661 and second 662 proximal ends, a distal end 663 and defines first 664 and second 665 lumens which converge into a third lumen 666. The first lumen 664 extends between an opening located at the first proximal end 661 and the third lumen 666 and is in communication with the third lumen 666. The second lumen 665 extends between an opening located at the second proximal end 662 and the third lumen 666 and is in communication with the third lumen 666. The third lumen 666 extends from the converging point of the first 664 and second 665 lumens to the distal end 663 of the adapter 660 and is in communication with the lumen 643 of the fitting 640. The first 661 and second 662 proximal ends include a connector 667 for releasably or fixedly connecting one or more elements and/or devices. The connectors 667 can include a sealing member to prevent fluid from flowing out of lumens 664 and 665 and/or provide a seal around any device traversing the adapter 660.

The distal end 663 of the adapter 660 is rotatably connected to the proximal end 641 of the fitting 640. Alternatively, the adapter 660 can be otherwise attached to the proximal end 641 of the fitting. An exemplary structure for rotatably connecting the adapter 660 to the fitting 640 is shown at 669, and includes a projection 643 and socket 670 configuration, as previously described herein.

While the adapter 660 has been illustrated as having a bifurcated configuration, the adapter 660 can include any suitable number of branches, and skilled artisans will be able to select an appropriate number of branches for inclusion in a light emitting irrigation device according to a particular embodiment based on various considerations, including the number of lumens defined by the elongate tubular member and/or fitting, and the intended use of the light emitting irrigation device. Examples of suitable numbers of branches for inclusion in an adapter include one, two, three, four and any number determined suitable for a particular application. For example, the adapter can comprise a single shaft defining one or more lumens in communication with one another or separate from one another.

The optical fiber 680 extends between proximal 682 and distal 684 ends and defines a light path extending through its length. The optical fiber 680 extends through the first lumen 664 and third lumen 666 of the adapter 660, through the lumen 643 of the fitting 640, through the lumen 623 of the elongate tubular member 620, and is disposed within the soft distal tip 626. The proximal end 682 of the optical fiber 680 is adapted to be operatively connected or attached to the light source 690. The distal end 684 of the optical fiber 680 is attached to soft distal tip 626. While the optical fiber 680 has been described and illustrated as extending through the first lumen 664 of the adapter 660, the optical fiber 680 can alternatively extend through the second lumen 665 of the adapter 660.

The light source 690 is operatively connected or attached to the proximal end 682 of the optical fiber 680 such that light generated by the light source 690 is able to travel through the light path defined by the optical fiber 680. While the light source 690 has been described and illustrated as attached to the proximal end 682 of the optical fiber 680, the light source 690 can alternatively be omitted from the irrigation device and provided separately.

The light emitting irrigation devices described and illustrated herein can be used in conjunction with a guidewire to assist in advancement of the device to a point of treatment. In addition, it is noted that all structure and features of the various described and illustrated elements can be combined and/or omitted in any suitable configuration for inclusion in a light emitting irrigation device. While particular configurations have been described and illustrated, skilled artisans will be able to select an appropriate configuration for a light emitting irrigation device according to a particular embodiment based on various considerations, including the intended use of the light emitting irrigation device, and the location of the treatment site, among others.

For example, an irrigation device can be adapted to include an elongate tubular member which omits the inclusion of a curve. In an additional example, the irrigation device can be adapted to omit the inclusion of a fitting and/or adapter, or adapted to include a fitting and/or adapter. In a further example, the elongate tubular member, adapter, and/or fitting can be adapted to include any suitable number of lumens in communication with one another or separate from one another. In another example, the irrigation device can be adapted to omit the inclusion of the light source.

Figure 7:
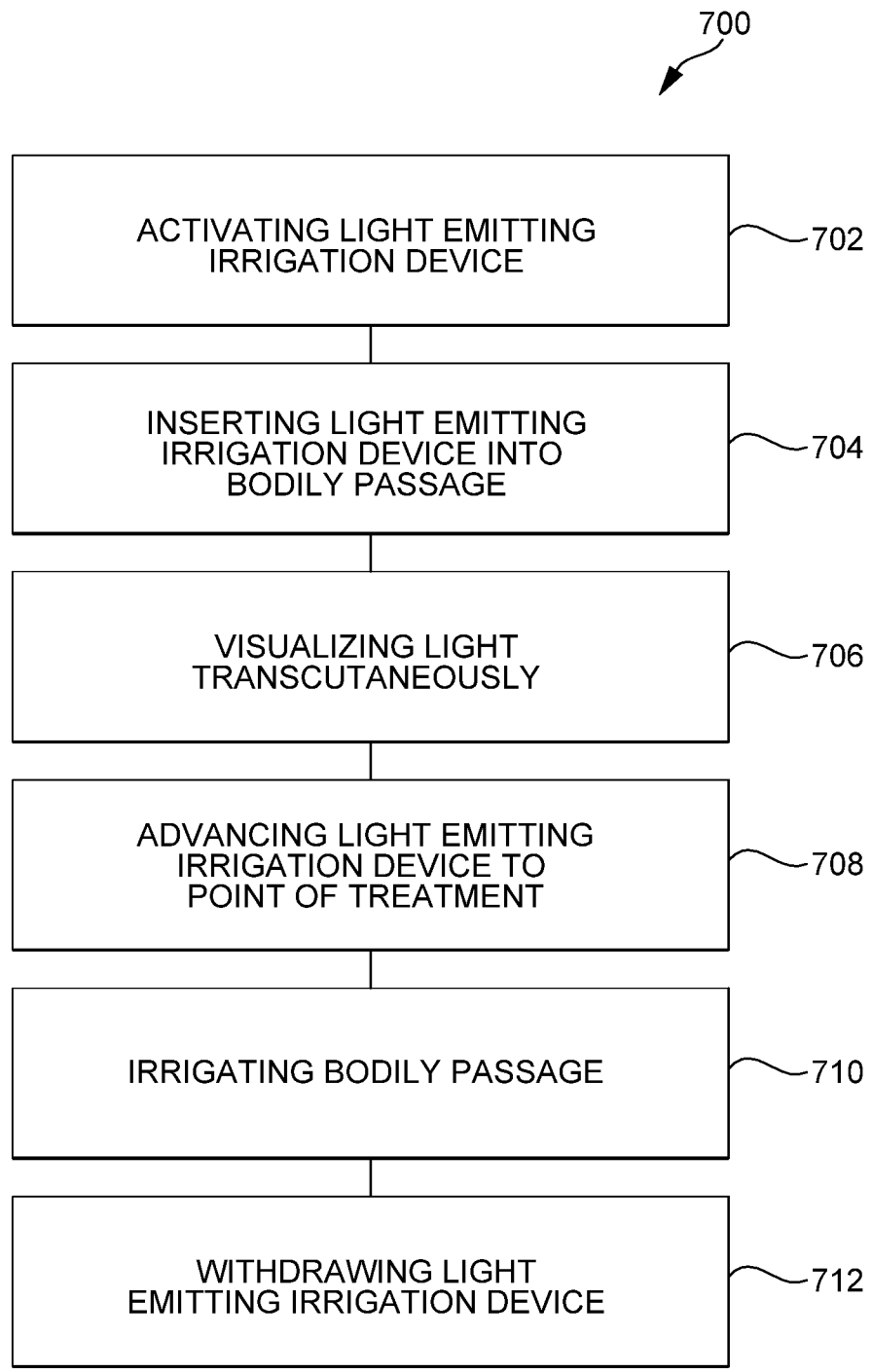
FIG. 7 is a flowchart representation of an exemplary method of treatment.

FIG. 7 is a flowchart representation of an exemplary method 700 of identifying and treating a bodily passage (e.g., a sinus cavity).

In the first step 702 a user activates a light emitting irrigation device according to an embodiment described herein, causing axially-directed light to travel through a light path defined by an optical fiber to emit from the distal end of the optical fiber.

In another step 704, a user inserts and advances the light emitting irrigation device into a bodily passage of a patient using conventional interventional techniques, such as by placing it on and advancing it over a previously-placed guidewire, or passing it through a guiding catheter to direct the light emitting irrigation device to a point of treatment. Alternatively, the user advances the light emitting irrigation device independent of any other device.

In another step 706, the user visualizes the axially-directed light transcutaneously, or by using a scope.

In another step 708, the user advances the distal end of the light emitting irrigation device into the portion of the bodily passage intended to be irrigated by visualizing the intensity of the axially-directed light and determining if the intensity of the axially-directed light is indicative of the positioning of the distal end of the light emitting irrigation device in the portion of the bodily passage intended to be treated.

In another step 710, the user irrigates the bodily passage. For example, in a sinus irrigation procedure, this step can be used to aspirate and/or flush a sinus cavity. When flushing the sinus cavity the user can use a variety of treatment materials, agents, and/or medications, such as saline, therapeutic agents, and the like. The treatment material can be injected into a portion of the light emitting irrigation device using a syringe or other device. The treatment material flows through the light emitting irrigation device and exits through the opening at its distal end and/or through one or more apertures. Examples of suitable treatment materials include drugs, bioactives, and/or other compounds, such as steroids, and/or anti-biotics, and/or any other suitable compound.

In another step 712, the user withdraws the light emitting irrigation device from the bodily passage.

Any of the light emitting irrigation devices described above with respect to FIGS. 1 through 6 can be used to assist in performing the above-described method 700. For example, the method 700 can comprise the use of a light emitting irrigation device as described above and illustrated in FIG. 1. Alternatively, the method 700 can comprise the use of a light emitting irrigation device as described above and illustrated in FIG. 2. Alternatively, the method 700 can comprise the use of a light emitting irrigation device as described above and illustrated in FIG. 3. Alternatively, the method 700 can comprise the use of a light emitting irrigation device as described above and illustrated in FIG. 4. Alternatively, the method 700 can comprise the use of a light emitting irrigation device as described above and illustrated in FIG. 5. Alternatively, the method 700 can comprise the use of a light emitting irrigation device as described above and illustrated in FIG. 6.

In addition, the method 700 can include various additional steps, as detailed above with respect to FIGS. 1 through 6. For example, an additional step of providing simultaneous flushing and suctioning can be incorporated within the above method. Alternatively, the flushing and suctioning can be provided separately, using separate irrigation ports and/or adapters.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A method of identifying and treating a bodily passage, the method comprising the steps of:
   activating a light source of an irrigation device such that the light source generates light, the irrigation device comprising:
      an elongate tubular member having a lengthwise axis and comprising a circumferential wall, a first proximal end, and a first distal end, the circumferential wall defining a first lumen extending between the first proximal end and the first distal end and a plurality of apertures, each aperture of the plurality of apertures extending through the circumferential wall and providing access to the first lumen; and
      an optical fiber disposed in the first lumen of the elongate tubular member and comprising a second proximal end operatively connected to the light source and a second distal end attached to the circumferential wall of the elongate tubular member at a point between the plurality of apertures and the distal end relative to the lengthwise axis, the optical fiber emitting light generated by the light source;
   inserting the irrigation device into said bodily passage;
   visualizing light emitted by the optical fiber;
   advancing the irrigation device to a point of treatment within said bodily passage;
   irrigating said bodily passage; and
   withdrawing the irrigation device from said bodily passage.

2. The method of claim 1, wherein the step of visualizing light emitted by the optical fiber comprises visualizing light emitted by the optical fiber transcutaneously.

3. The method of claim 1, wherein the optical fiber emits light radially such that radially-directed light is emitted through the plurality of apertures; and wherein the step of visualizing light emitted by the optical fiber comprises visualizing radially-directed light emitted by the optical fiber.

4. The method of claim 1, wherein the optical fiber emits light axially such that axially-directed light is emitted from the second distal end of the optical fiber; and wherein the step of visualizing light emitted by the optical fiber comprises visualizing axially-directed light emitted by the optical fiber.

5. The method of claim 1, further comprising the step of aspirating said bodily passage.

6. The method of claim 5, wherein the step of irrigating said bodily passage and the step of aspirating said bodily passage are completed simultaneously.

7. The method of claim 1, wherein the step of inserting the irrigation device into said bodily passage is completed independent of any other device.

8. The method of claim 1, wherein the elongate tubular member defines a curve along the lengthwise axis;

wherein each aperture of the plurality of apertures is defined by the circumferential wall at a point between the curve and the first distal end.

9. The method of claim 1, further comprising an adapter disposed on the first proximal end of the elongate tubular member, the adapter comprising third proximal and distal ends, a fourth proximal end, and defining second and third lumens, the third distal end of the adapter connected to the first proximal end of the elongate tubular member, the second lumen extending between the third proximal end and the third distal end, and the third lumen in communication with the second lumen and extending between the fourth proximal end and the second lumen.

10. The method of claim 9, wherein the third distal end of the adapter is rotatably connected to the first proximal end of the elongate tubular member.

11. The method of claim 1, wherein a portion of the second distal end of the optical fiber is disposed distal to the first distal end of the elongate tubular member.

12. The method of claim 1, wherein at least two apertures of the plurality of apertures have different diameters.

13. The method of claim 1, wherein the step of inserting the irrigation device into said bodily passage comprises inserting the irrigation device into a sinus cavity;

wherein the step of advancing the irrigation device to a point of treatment within said bodily passage comprises advancing the irrigation device to a point of treatment within the sinus cavity;

wherein the step of irrigating said bodily passage comprises irrigating the sinus cavity; and wherein the step of withdrawing the irrigation device from said bodily passage comprises withdrawing the irrigation device from the sinus cavity.

14. A method of identifying and treating a sinus cavity, the method comprising the steps of:

activating a light source of an irrigation device such that the light source generates light, the irrigation device comprising:

an elongate tubular member having a lengthwise axis and comprising a circumferential wall, a first proximal end, and a first distal end, the circumferential wall defining a first lumen extending between the first proximal end and the first distal end and a plurality of apertures, each aperture of the plurality of apertures extending through the circumferential wall and providing access to the first lumen; and an optical fiber disposed in the first lumen of the elongate tubular member and comprising a second proximal end operatively connected to the light source and a second distal end attached to the circumferential wall of the elongate tubular member at a point between the plurality of apertures and the distal end relative to the lengthwise axis, the optical fiber emitting light generated by the light source axially such that axially-directed light is emitted from the second distal end of the optical fiber;

inserting the irrigation device into said sinus cavity;

visualizing axially-directed light emitted by the optical fiber transcutaneously;

advancing the irrigation device to a point of treatment within said sinus cavity;

irrigating said sinus cavity; and withdrawing the irrigation device from said sinus cavity.

15. The method of claim 14, wherein the optical fiber emits light radially such that radially-directed light is emitted through the plurality of apertures; and wherein the step of visualizing axially-directed light emitted by the optical fiber transcutaneously comprises visualizing axially-directed light and radially-directed light emitted by the optical fiber transcutaneously.

16. The method of claim 14, further comprising the step of aspirating said sinus cavity.

17. The method of claim 16, wherein the step of irrigating said sinus cavity and the step of aspirating said sinus cavity are completed simultaneously.

18. The method of claim 14, further comprising an adapter disposed on the first proximal end of the elongate tubular member, the adapter comprising third proximal and distal ends, a fourth proximal end, and defining second and third lumens, the third distal end of the adapter connected to the first proximal end of the elongate tubular member, the second lumen extending between the third proximal end and the third distal end, and the third lumen in communication with the second lumen and extending between the fourth proximal end and the second lumen.

19. The method of claim 18, wherein the third distal end of the adapter is rotatably connected to the first proximal end of the elongate tubular member.

20. A method of identifying and treating a sinus cavity, the method comprising the steps of:

activating a light source of an irrigation device such that the light source generates light, the irrigation device comprising:

an elongate tubular member having a lengthwise axis and comprising a circumferential wall, a first proximal end, and a first distal end, the circumferential wall defining a first lumen extending between the first proximal end and the first distal end and a plurality of apertures, each aperture of the plurality of apertures extending through the circumferential wall and providing access to the first lumen; and an optical fiber disposed in the first lumen of the elongate tubular member and comprising a second proximal end operatively connected to the light source and a second distal end attached to the circumferential wall of the elongate tubular member at a point between the plurality of apertures and the distal end relative to the lengthwise axis, the optical fiber emitting light generated by the light source axially such that axially-directed light is emitted from the second distal end of the optical fiber and radially such that radially-directed light is emitted through the plurality of apertures;
inserting the irrigation device into said sinus cavity;
visualizing axially-directed light and radially-directed light emitted by the optical fiber transcutaneously;
advancing the irrigation device to a point of treatment within said sinus cavity;
irrigating said sinus cavity;
aspirating said sinus cavity; and
withdrawing the irrigation device from said sinus cavity.

* * * * *